United States Patent
Nawar

(10) Patent No.: US 6,641,847 B1
(45) Date of Patent: Nov. 4, 2003

(54) CRANBERRY SEED OIL EXTRACT AND COMPOSITIONS CONTAINING COMPONENTS THEREOF

(75) Inventor: Wassef W. Nawar, Amherst, MA (US)

(73) Assignee: Ocean Spray Cranberries, Inc., Lakeville-Middleboro, MA (US)

(*) Notice: Subject to any disclaimer, the term of this patent is extended or adjusted under 35 U.S.C. 154(b) by 0 days.

(21) Appl. No.: 09/586,684

(22) Filed: Jun. 1, 2000

Related U.S. Application Data

(60) Provisional application No. 60/137,405, filed on Jun. 1, 1999.

(51) Int. Cl.⁷ .............................................. A61K 35/78
(52) U.S. Cl. ...................................... 424/732; 424/776
(58) Field of Search ................................ 424/732, 776

(56) References Cited

U.S. PATENT DOCUMENTS

| | | | |
|---|---|---|---|
| 4,603,142 A | | 7/1986 | Burger et al. |
| 5,525,341 A | * | 6/1996 | Walker et al. |
| 5,591,772 A | | 1/1997 | Lane et al. |
| 5,646,178 A | * | 7/1997 | Walker et al. |
| 5,766,571 A | * | 6/1998 | Ceriani et al. |
| 6,391,345 B1 | | 5/2002 | Heeg et al. |
| 2002/0168430 A1 | | 11/2002 | Heeg et al. |

FOREIGN PATENT DOCUMENTS

| | | | |
|---|---|---|---|
| EP | 421419 | | 4/1991 |
| EP | 834261 | | 4/1998 |
| WO | WO 99/12541 | * | 3/1999 |
| WO | WO 99/15167 | | 4/1999 |
| WO | WO 99/55350 | | 11/1999 |

OTHER PUBLICATIONS

Borradaile et al., "Regulation of HepG2 cell Apolipoprotein B metabolism by the citrus flavanones hesperetin and naringenin," *Lipids* Jun.1999;34(6):591–8.

Carroll et al., "Dietary fatty acids, tocotrienols and cancer," *Lipids* 5:141–147 (1998).

Carroll et al., "Anticancer properties of flavonoids, with emphasis on citrus flavonoids," In *Flavonoids in health and disease*; Rice–Evans, Packer (Eds.), Marcel Dekker, Inc., New York pp. 437–446 (1998).

Chen, Y., "Volatile components and oxidative stability of cranberry seed oil," Thesis submitted to the Graduate School of the University of Massachusetts Amherst, Feb. 1997.

Cook et al., "Flavonoids—chemistry, metabolism, cardioprotective effects and dietary source," *J. Nutr. Biochem.* 7:66–76 (1996).

Fukuzawa et al., "Increased platelet–activating factor (PAF) synthesis in polymorphonuclear leukocytes of vitamin E–deficient rats," *Annals of the New York Academy of Sciences*, 570:449–453 (1989).

Guthrie et al., "Palm oil tocotrienols and plant flavonoids act synergistically with each other and with tamoxifen in inhibiting proliferation and growth of estrogen receptor–negative MDA–MB–435 and –positive MCF–7 human breast cancer cells in culture," *J. Clin. Nutr.* 6(1):41–45 (1997).

Guthrie et al., "Inhibition of proliferation of estrogen receptor–negative MDA–MB–435 and –positive MCF–7 human breast cancer cells by palm oil tocotrienols and tamoxifen, alone and in combination," *J. Nutr.* Mar.1997;127(3):544S–548S.

Guthrie et al., "Tocotrienols and cancer," in: *Biological Oxidants: Molecular Mechanisms and Health Effects*, Packer and Augustine Eds., AOCS Press, Champaign, Illinois pp. 257–264 (1998).

Guthrie et al., "Inhibition of mammary cancer by citrus flavonoids," In *Flavonoids in the living system* Manthey and Buslig Eds. Plenum Press, New York pp. 227–236 (1998).

Guthrie et al., "Inhibition of human breast cell growth and metastasis in nude mice by citrus juices and their constituent flavonoids," In *Flavonoids in health and disease*, Rice–Evans and Packer Eds., Marcel Dekker, Inc., New York, New York pp. 310–316 (1998).

Hertog et al., "Intake of potentially anticarcinogenic flavonoids and their determirants in adults in the Netherlands," *Nutr. Cancer* 20:21–29 (1993).

Kurowaska et al., "Role of tocotrienols from palm oil in regulation of Apo B metabolism in HepG2 cells," *FASEB*, 13(4):A562 (1999) (Abs.).

Middeleton et al., "The flavonoids" *Trends Pharm. Sci.*, 5:335–338 (1984).

Niki et al., "Inhibition of oxidation of biomembranes by tocopherol," *Annals of the New York Academy of Sciences*, 570:23–31 (1989).

Osborne et al., "Comparison of the effects of a pure steroidal antiestrogen with those of tamoxifen in a model of human breast cancer," *J. Natl. Cancer Inst.* 87:746–750 (1995).

Qureshi et al., "Suppression of cholesterogenesis by plant constituents: review of Wisconsin contributions to NC–167," *Lipids*, 20:817–824 (1985).

(List continued on next page.)

*Primary Examiner*—Francisco Prats
*Assistant Examiner*—Susan D Coe
(74) *Attorney, Agent, or Firm*—Lahive & Cockfield, LLP; Jane E. Remillard, Esq.; Peter W. Dini

(57) ABSTRACT

Isolated cranberry seed oil and components thereof, in a form suitable for use as a foodstuff, dietary supplement, or pharmaceutical composition, are disclosed. The isolated cranberry seed oil or compositions comprising one or a combination of components derived from the cranberry seed oil can be used as anticancer, hypocholesterolemic, antithrombotic, antioxidizing, antiatherogenic, antiinflammatory, and immunoregulatory agents. In addition, the invention features novel methods of extracting cranberry seed oil from cranberry seeds in a form suitable for adding to foodstuffs, dietary supplements, or pharmaceutical compositions.

11 Claims, 10 Drawing Sheets

OTHER PUBLICATIONS

Qureshi et al., "The structure of an inhibitor of cholesterol biosynthesis isolated from barley," *J. Biol. Chem.*, 261:10544–550 (1986).

Qureshi et al., "Lowering of serum cholesterol in hypercholesterolemic humans by tocotrienols (palmvitee)," *Am. J. Clin. Nutr.*, 53:1021S–6S (1991).

So et al., "Inhibition of human breast cancer cell proliferation and delay of mammary tumorigenesis by flavonoids and citrus juices" *Nutr. Cancer* 26:167–181 (1996).

So et al., "Inhibition of proliferation of estrogen receptor–positive MCF–7 human breast cancer cells by flavonoids in the presence and absence of excess estrogen" *Cancer Letters*, 112:127–133 (1997) and corrigendum.

Wilcox et al., "Naringenin, a citrus flavanoid, markedly decreases Apo B secretion in HepG2 cells and inhibits acyl CoA: cholesterol acyltransferase," *Circulation*, 98(17):I–537 (1998) (abs.).

Croteau, Rodney and fagerson, Irving S. "Seed Lipids of the American Cranberry" *Phytochemistry* 8(11):2219–22 (1969).

Heinonen, I. Marina et al. "Antoxidant of Berry and Fruit Wines and liquors" *J. Agricultural &Food Chemistry* 46(1):25–31 (1998).

Wang, Shiow Y. et al. "Ellagic Acid Content in Small Fruits, Mayhaws, and Other Plants" *J. Small Fruit & Viticulture* 2(4):39–49 (1994).

* cited by examiner

|       |              | $R_1$ | $R_2$ | $R_3$ |
|-------|--------------|-------|-------|-------|
| α-T₃  | α-tocotrienol | CH₃  | CH₃  | CH₃  |
| β-T₃  | β-tocotrienol | CH₃  | H    | CH₃  |
| γ-T₃  | γ-tocotrienol | H    | CH₃  | CH₃  |
| δ-T₃  | δ-tocotrienol | H    | H    | CH₃  |

|      |              | $R_1$ | $R_2$ | $R_3$ |
|------|--------------|-------|-------|-------|
| α-T  | α-tocopherol | CH₃  | CH₃  | CH₃  |
| β-T  | β-tocopherol | CH₃  | H    | CH₃  |
| γ-T  | γ-tocopherol | H    | CH₃  | CH₃  |
| δ-T  | δ-tocopherol | H    | H    | CH₃  |

CRANBERRY SEED OIL EXTRACT AND COMPOSITIONS CONTAINING COMPONENTS THEREOF

RELATED INFORMATION

This application claims priority to U.S. provisional Application No. 60/137,405, entitled "CRANBERRY SEED OIL EXTRACT AND COMPOSITIONS CONTAINING COMPONENTS THEREOF," filed on Jun. 1, 1999, incorporated herein in its entirety by this reference. The contents of all patents, patent applications, and references cited throughout this specification are hereby incorporated by reference in their entireties.

BACKGROUND OF THE INVENTION

For millennia, humankind has relied on plant derivatives for the prevention and treatment of a wide variety of aliments. For example, in China, various teas have been used as a crude medicine for over 4,000 years. And more recently, there has been considerable interest in taking advantage of various plant extracts as a source of health promoting substances such as, natural oxidants, flavonoids, and phenolic compounds. In part, this trend is due to a growing body of evidence demonstrating that some of these compounds have beneficial properties that may be advantageous in preventing or delaying, for example, the onset of cardiovascular disease.

Indeed, several studies have suggested that beneficial fatty acid and other plant derived compounds have desirable effects ranging from reducing lipid levels, lowering blood pressure, and regulating inflammatory disease. For example, barley has been shown to be particularly effective in lowering lipid levels in test animals (Quereshi et al., *Lipids*, 20:817–24 (1985)). And in particular, a tocochromanol isolated from barley extract has been identified as an active compound suitable for treating hypercholesterolemia (Quereshi et al., *J. Biol. Chem.*, 261:10544–50 (1986)). Similarly, other tocochromanols, for example, γ-tocotrienol and δ-tocotrienol have also been shown to reduce hypercholesterolemia in mammals (European patent application 421,419).

In general, hypercholesterolemia involves high serum cholesterol levels that are associated with a number of diseases including atherosclerosis, arteriosclerosis, and cardiovascular disease. In addition, high serum cholesterol levels are also seen in patients suffering from other diseases such as diabetes mellitus and familial hypercholesterolemia. While improvement of lipoprotein profiles and a decrease in total serum and low density lipoprotein cholesterol have been shown to slow the progression of such diseases, the exact link between hypercholesterolemia and, most notably, cardiovascular disease, has remained obscure. As a result, cardiovascular disease continues to remain a leading cause of death in the United States.

In part, the reason a cure for cardiovascular disease has remained elusive, is that the etiology of the disease may be the result of series of complex interactions involving genetic factors, lipoprotein metabolism, clotting functions, and even lifestyle choices (e.g., diet, exercise). Interestingly, populations consuming large amounts of cereal grains have a lower incidence of cardiovascular disease and lower cholesterol levels. Studies looking at the beneficial properties of cereal diets have attributed these effects to naturally occurring tocochromanols, and these compounds have been found in a wide variety of plant sources (Quereshi et al., *Am. J. Clin. Nutr.*, 53:1021S–6S (1991)).

As a class of compounds, tocochromanols include the tocopherols and the tocotrienols. Tocopherols, including δ-α-tocopherol are essentially the active ingredient in vitamin E and have been extensively studied. A number of beneficial properties have been attributed to the tocopherols such as reduced platelet aggregation and antioxidant functions (Niki et al., *Annals of the New York Academy of Sciences*, 570:23–31 (1989); Fukuzawa et al., *Annals of the New York Academy of Sciences*, 570:449–453 (1989)).

The tocotrienols have been less well studied although recent evidence suggests that these compounds may also be biologically active (see for example U.S. Pat. No. 5,591,772 and 4,603,142). Naturally occurring tocotrienols including α- β-, γ-, and δ-tocotrienol have been identified in and isolated from a variety of sources including, e.g., rice, rice bran, barley, coconut, and palm. These compounds exhibit varying degrees of hypercholesterolemic activity and have also been used as antithrombotic agents and antioxidants.

Additional sources of tocopherols, tocotrienols, and other therapeutically beneficial compounds which can be used safely and effectively, for example, as a hypercholesterolemic, antithrombotic, antioxidizing, antiatherogenic, antiinflammatory, and immunoregulatory agents, would be of great benefit.

SUMMARY OF THE INVENTION

The present invention provides isolated cranberry seed oil, a novel source of health promoting compounds (e.g., desirable fatty acids, tocochromanols) that are useful in a variety of therapeutic applications, for example, as a hypocholesterolemic, antithrombotic, antioxidizing, antiatherogenic, antiinflammatory, and immunoregulatory agents. In addition, the invention provides methods of efficiently extracting cranberry seed oil to a high level of purity from cranberry seeds, for example, such that the extract can be added to foodstuffs or used as a dietary supplement or a pharmaceutical composition.

Accordingly, in one aspect, the invention provides an isolated cranberry seed oil extract which is substantially free of impurities. The extract can contain, for example, α-tocopherol, γ-tocopherol, δ-tocopherol, α-tocotrienol, γ-tocotrienol, δ-tocotrienol, or a combination thereof. In another embodiment, the extract further comprises an exogenous flavonoid, tamoxifen, or a combination thereof. In a related embodiment, the flavonoid is a flavone, flavavone, isoflavone, or flavonol. In another embodiment, the extract further comprises a fatty acid, preferably, α-linolenic acid (omega-3), oleic acid (omega-9), linoleic acid (omega-6), or a combination thereof. In another embodiment, the extract further comprises a sterol, preferably, β-sitosterol, schottenol (i.e., stigmastenol), or a combination thereof.

In another embodiment, the extract further comprises a triterpene alcohol, such as α-amyrin, β-amyrin, 24-methylene parkeol, or a combination thereof. In still another embodiment, the extract further includes a phenolic compound, preferably, methoxyphenylpropionic acid, methoxycinnamic acid, or a combination thereof.

In another aspect, the invention provides a therapeutic composition (e.g. a foodstuff, dietary supplement, or pharmaceutical composition) comprising isolated cranberry seed oil or one or a combination of the above listed compounds derived from cranberry seed oil. Accordingly, the composition can contain one or more of the following components: a tocochromanol (e.g., α-tocopherol, γ-tocopherol, δ-tocopherol, α-tocotrienol, γ-tocotrienol, δ-tocotrienol, or a combination thereof), an exogenous flavonoid (e.g., flavone, flavavone, isoflavone, or flavonol) a fatty acid (e.g., α-linolenic acid (omega-3), oleic acid (omega-9), linoleic acid (omega-6), or a combination thereof), a sterol (e.g., βsitosterol, schottenol (i.e., stigmastenol), or a combination thereof), a triterpene alcohol (e.g., α-amyrin, β-amyrin, 24-methyleneparkeol, or a combination thereof), or a phenolic compound (e.g., methoxyphenylpropionic acid, methoxycinnamic acid, or a combination thereof).

In another aspect, the invention provides a method for treating or preventing a disease or condition in a subject such as a malignancy, a hypercholesterolemic-related disease, a thrombotic disease, a respiratory disease, an atherogenic disease, an inflammatory disease or condition, a neurological disease, a dermatological disease, an opthalmological disease, or a gastroenterological disease, by administering to the subject a therapeutically-effective amount of a therapeutic composition (e.g., foodstuff, dietary supplement, or pharmaceutical composition) of the invention.

In a related embodiment, the subject has, or is at risk for acquiring, a malignancy, and is administered a composition comprising a tocotrienol, a flavonoid, tamoxifen, or a combination thereof.

In another related embodiment, the subject has or is at risk for acquiring a hypocholesterolemic-related disease, and is administered a composition comprising α-tocopherol, α-tocotrienol, γ-tocotrienol, δ-tocotrienol, or a combination thereof.

In yet another related embodiment, the subject has, or is at risk for acquiring, a respiratory disease, an inflammatory disease, a neurological disease, a derrnatological disease, an opthalmological disease, or a gastroenterological disease and is administered a composition comprising α-tocopherol.

In another aspect, the invention provides a method for treating, preventing, or lowering the risk of acquiring a disorder or condition associated with an alteration in membrane stability, membrane fluidity, 5-lipoxygenase activity, or protein kinase C activity in a subject containing, the step of administering to the subject a therapeutically-effective amount of a therapeutic composition (e.g., foodstuffs, dietary supplements, or pharmaceutical compositions) of the invention.

In another aspect, the invention provides a method for nutritionally supplementing a foodstuff by adding to the foodstuff an isolated extract, or one or more components derived therefrom. Accordingly, in one embodiment, the foodstuff, comprises a tocochromanol (e.g., α-tocopherol, γ-tocopherol, δ-tocopherol, α-tocotrienol, γ-tocotrienol, δ-tocotrienol, or a combination thereof) an exogenous flavonoid (e.g., flavone, flavavone, isoflavone, or flavonol), tamoxifen, or a combination thereof, a fatty acid (e.g., α-linolenic acid (omega-3), oleic acid (omega-9), linoleic acid (omega-6), or a combination thereof), a sterol (e.g., β-sitosterol, schottenol (i.e., stigmastenol), or a combination thereof), a triterpene alcohol (e.g., α-amyrin, β-amyrin, 24-methylene parkeol, or a combination thereof), or a phenolic compound (e.g., methoxyphenylpropionic acid, methoxycinnamic acid, or a combination thereof).

In another aspect, the invention provides a method for isolating cranberry seed oil to a high level of purity, for example, so that the cranberry seed oil or components thereof can be administered to a patient or to an animal as a therapeutic. In one embodiment, the method involves physically disrupting cranberry seeds, adding to the seeds an organic solvent to produce an extract/solvent mixture, separating the extract/solvent mixture from the cranberry seeds, and removing the solvent portion of the extract/solvent mixture resulting in an isolated cranberry seed oil essentially free of solvent. In a preferred embodiment, the organic solvent is hexane and the adding step is conducted at a temperature between 50° and 90° F., and, more preferably, at a temperature between 50° and 65° F. In another embodiment, the separating step includes an extract receiver maintained at room temperature and atmospheric pressure. In another embodiment, the removing step is conducted at a temperature between 30° and 220° F. and under vacuum, preferably, a vacuum pressure of 22 inches of Hg or greater. In one embodiment, the extraction method results in an extraction yield by weight that is at least 10% or greater, preferably 15% or greater, and more preferably, at least 20% of the total weight of original seed or greater. In another embodiment, the extraction method also includes the step of increasing the oxidative stability of the resultant extract, by exposing the extract to ascorbic acid, BHT, low temperature, or a combination of these conditions.

In a related aspect, the invention provides isolated cranberry seed oil produced by the above-mentioned extraction method. Accordingly, the cranberry seed oil is substantially free of impurities. In one embodiment, the isolated cranberry seed oil contains a tocochromanol (e.g., a α-tocopherol, γ-tocopherol, β-tocopherol, α-tocotrienol, γ-tocotrienol, β-tocotrienol, or a combination thereof), an exogenous flavonoid, an exogenous tamoxifen, a fatty acid (e.g., α-linolenic acid (omega-3), oleic acid (omega-9), linoleic acid (omega-6)), a sterol (e.g., β-sitosterol, schottenol (i.e., stigmastenol), α-amyrin, β-amyrin, 24-methylene parkeol), a phenolic compound (e.g., methoxyphenylpropionic acid, methoxycinnamic acid, or a combination thereof) or any combination of the above components. In a related embodiment, the isolated cranberry seed oil is contained in a foodstuff, dietary supplement, or pharmaceutical composition. Accordingly, in another aspect, the invention provides a foodstuff, dietary supplement, or pharmaceutical composition comprising isolated cranberry seed oil, or one or more components thereof, produced by a method of the invention.

DETAILED DESCRIPTION OF THE INVENTION

Figure 1:
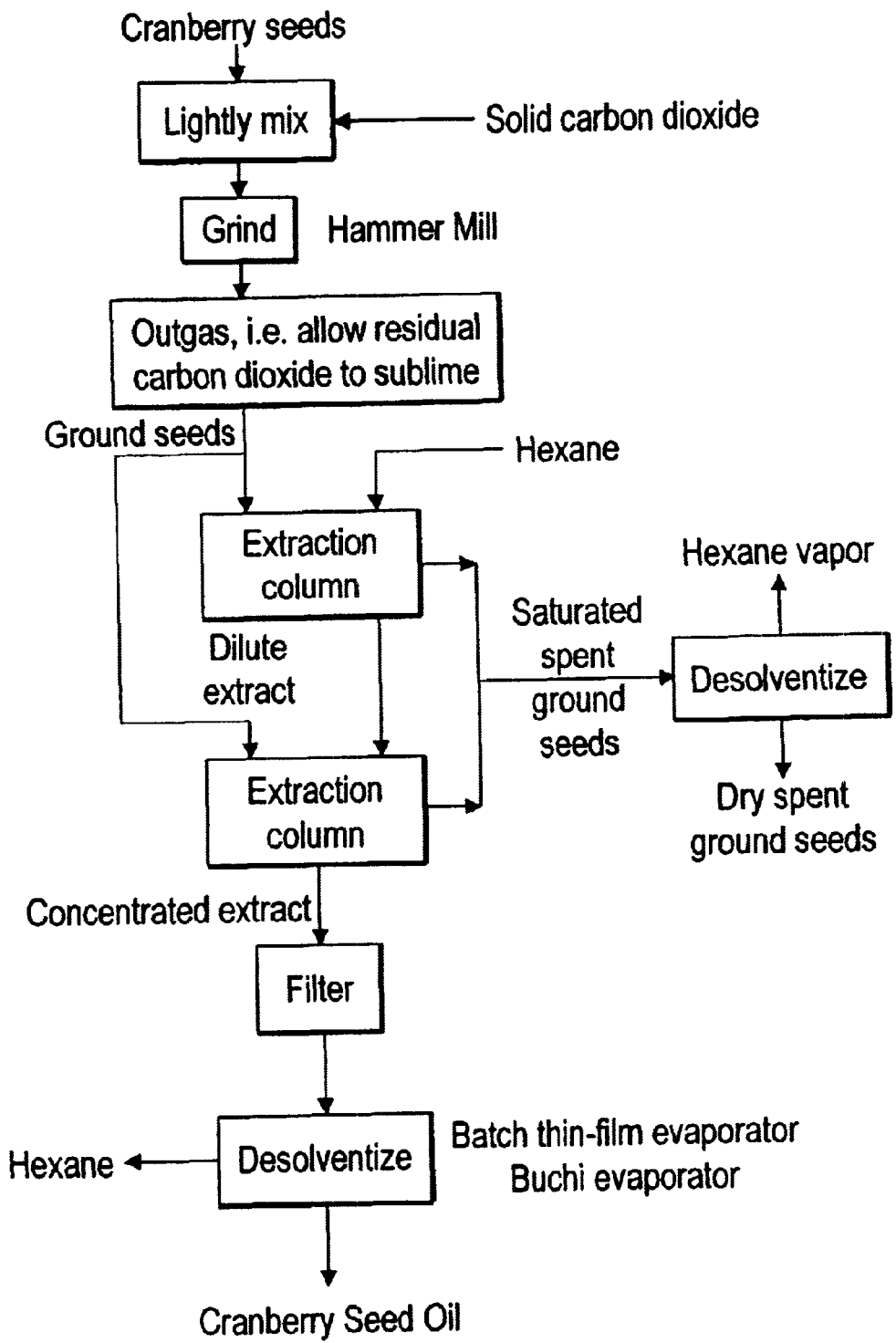
FIG. 1 shows a flow chart for extracting cranberry seed oil from cranberry seeds. The method shown is particularly suitable for small scale production of cranberry seed oil.

The invention provides an isolated and highly pure cranberry seed oil extract, a novel source of several therapeutically beneficial compounds, which can be administered to animals or humans, for example, in the form of a foodstuff, dietary supplement, or pharmaceutical composition. Accordingly, in particular embodiments, the invention features a foodstuff, dietary supplement, or pharmaceutical composition comprising isolated cranberry seed oil or one or a combination of components derived therefrom. The invention also provides methods for efficiently extracting cranberry seed oil from cranberry seeds to a high level of purity.

These and other elements of the invention are described below.

Definitions

As used herein, the term "isolated" refers to cranberry seed oil isolated from its natural context (i.e., cranberry seeds). "Isolated cranberry seed oil" and "cranberry seed oil extract" are used interchangeably herein. Preferably, "isolated cranberry seed oil" of the invention has high stability against oxidation, good light-golden color, long shelf life, resistance to gelling, a pleasant flavor, a high tocochromanol content (especially tocotrienols having anti-carcinogenic properties), rich in omega-3-acid alpha linolenic acid, and is substantially free of free fatty acids (especially, saturated fatty acids, e.g., palmitic acid, known to be a major contributor to heart disease) and impurities.

The terms "substantially free of impurities" and "high level of purity" refers to cranberry seed oil which is substantially (e.g., at least 80–90%, preferably 90–99%, more preferably greater than 99%, and most preferably greater than 99.7%) free of solvent as determined by smell and gas chromatography, free of peroxides (as determined by a very low peroxide value, e.g., less than 7 meq/Kg), free of free fatty acids (as determined by titration, e.g., less than 0.8% oleic), free of solids, e.g., hull and other particles (e.g., as determined by a crystal clear appearance), and/or off-flavors (as determined by taste and smell).

The term "tocochromanol" refers to any tocopherol (T) or tocotrienol (T3) compound, for example, α-tocopherol, γ-tocopherol, δ-tocopherol, α-tocotrienol, γ-tocotrienol, δ-tocotrienol, or a combination thereof, that is present in measurable levels in cranberry seeds.

The term "native" means the component is derived from cranberry seed.

The term "exogenous" means the component is derived or obtained from a source other than cranberry seeds. Exogenous compounds suitable for adding to a cranberry seed oil extract include, for example, tamoxifen, and various flavonoids (e.g., a flavone, a flavavone, a isoflavone, or a flavonol).

The term "fatty acid" refers to a fatty acid that is naturally present at some measurable level in cranberry seeds and includes, for example, α-linolenic acid (omega-3), oleic acid (omega-9), linoleic acid (omega-6), or a combination thereof.

The term "sterol" refers to any sterol (e.g., that is naturally present at some measurable level in cranberry seeds (there are at least 60 of which 14 have been characterized)) and includes, for example, βsitosterol and schottenol (i.e., stigmastenol).

The term "triterpene alcohol" refers to a triterpene alcohol (e.g., that is naturally present at some measurable level in cranberry seeds (there are at least 22, of which 7 have been identified)), and includes, for example, α-amyrin, β-amyrin, and 24-methylene parkeol.

The term "phenolic compound" refers to a phenolic compound (e.g., that is naturally present at some measurable level in cranberry seeds) and includes, for example, methoxyphenylpropionic acid and methoxycinnamic acid.

The term "foodstuff" refers to any edible substance that can be used as or in food for an animal or human. Foodstuffs include substances that may be used in the preparation of foods such as cooking oils or food additives. Foodstuffs also include animals or animal products used for human consumption, such as, for example eggs or milk. Such animal themselves can be fed or treated with a composition of the invention and retain the advantageous properties of the composition (e.g., isolated cranberry seed oil or components thereof) or impart those advantageous properties to products such as eggs or milk.

The term "dietary supplement" refers to a compound or composition used to supplement the diet of an animal or human.

The term "pharmaceutical composition" refers to a composition formulated for therapeutic use.

The term "major components" refers to a component generally found in the extracts of the invention in amounts greater than 1% by weight (e.g., a fatty acid).

The term "minor components" or "trace components" refers to a component generally found in the extracts of the invention in amounts less than 1% by weight (e.g., sterols, triterpene alcohols, phenolic compounds, and tocochromanols).

Cranberry Seed Oil (CSO) Extract and its Components

Cranberry seed oil (CSO) extracts of the invention provide a novel source of several therapeutically beneficial compounds, such as omega-3, omega-6, and omega-9 fatty acids, tocochromanols and sterols. CSO extracts of the invention also provide several advantages over currently known sources of such therapeutically beneficial compounds including, for example, a remarkably high concentration of particularly desirable components (e.g., omega-3 fatty acids, tocochromanols and sterols), low levels of undesirable fatty acids (e.g., palmitic oil), and a high level of purity, for example, so that the CSO or components thereof can be used in foodstuffs, or as dietary supplement or pharmaceutical composition.

Accordingly, in one embodiment, the invention provides a CSO extract, or a composition comprising one or more major and/or minor components of a CSO extract, as listed in Table 1, which promotes health in a human or other animal. The CSO extract or composition derived therefrom is also preferably substantially free of impurities and low in undesirable fatty acids. The CSO extract or composition derived therefrom also can contain one or more exogenous (i.e., externally added) compounds to further enhance the therapeutic value of the CSO extract or composition derived therefrom, for example, by acting in synergism with one or more native components of the CSO extract.

The terms "health promoting", "therapeutic" and "therapeutically active" are used interchangeably herein, and refer to the prevention or treatment of a disease or condition in a human or other animal, or to the maintenance of good health in a human or other animal, resulting from the administration of a CSO extract of the invention, or a composition derived therefrom. Such health benefits can include, for example, nutritional, physiological, mental and neurological health benefits.

As shown in Table 1 (below), CSO extracts of the invention can contain one or more of the following compounds: fatty acids, e.g., α-linolenic acid (omega-3), oleic acid (omega-9), and linoleic acid (omega-6); sterols, e.g., β-sitosterol or schottenol (i.e., stigmastenol); triterpene alcohols, e.g., α-amyrin, β-amyrin, or 24-methylene parkeol; phenolic compounds, e.g., methoxyphenylpropionic acid, and methoxycinnamic acid; tocochromanols, e.g., α-tocopherol, γ-tocopherol, δ-tocopherol, α-tocotrienol, γ-tocotrienol, and δ-tocotrienol. In addition, exogenous compounds, such as flavonoids and/or tamoxifens, can be added to CSO extracts of the invention and compositions derived therefrom, to achieve a synergistic effect.

TABLE 1

Major and Minor Components of Cranberry Seed Oil

| MAJOR COMPONENTS | MINOR (TRACE) COMPONENTS |
|---|---|
| 1. Omega-3 Fatty Acids<br>α-linolenic acid (33%) | 1. Sterols, 60 detected, 14 identified, 2 characterized (0.12%)<br>B-sitosterol (delta-5) |
| 2. Omega-6 Fatty Acids<br>Linoleic acid (38%) | Schottenol (stigmastenol) (delta-7)<br>2. Triterpene Alcohols, 22 detected, 7 identified, 3 characterized (0.6%) |
| 3. Omega-9 Fatty Acids<br>Oleic acid (21%) | α-amyrin<br>β-amyrin<br>24-methylene parkeol<br>3. Phenolic Compounds, 2 characterized<br>methoxyphenylpropionic acid<br>methoxycinnamic acid<br>4. Tocopherols<br>α-tocopherol ~130 ppm<br>β-tocopherol ~ trace<br>γ-tocopherol 110 ppm<br>δ-tocopherol 16 ppm<br>5. Tocotrienols<br>α-tocotrienol ~180 ppm<br>β-tocotrienol 0 ppm<br>γ-tocotrienol 1,500 ppm<br>δ-tocotrienol 50 ppm |

*Percentages (%) are by weight
*ppm = parts per million

I. Major Components

One class of major components found in cranberry seed oil extracts of the invention are the fatty acids. In particular, cranberry seed oil extracts of the invention are rich in omega-3, omega-6, and omega-9 fatty acids. Typically, the cranberry seed oil extract contains, by weight, approximately 30–38%, (typically about 33%) α-linolenic acid (omega-3), 35–39% (typically about 38%) linoleic acid (omega-6), and 20–22% (typically about 21%) oleic acid (omega-9). Moreover, cranberry seed oil extracts of the invention have the additional advantages of being edible, having a pleasant flavor, and preferably having good oxidative stability.

In contrast, other known sources of fatty acids lack these advantages. For example, flaxseed oil (linseed oil) is not an edible oil, but rather a "drying" oil used in the painting industry. Oils from soybean, fish, rapeseed, and canola lack the pleasant flavor and the presence of beneficial tocotrienols. In addition, fish oil lacks the stability against oxidation exhibited by cranberry seed oil. Moreover, none of these oils have the superior combination of therapeutic compounds found in cranberry seed oil. Specifically, while these oils have omega-3 fatty acids, isolated cranberry seed oil of the invention also has both omega-6 and omega-9 fatty acids which play important roles in various health aspects.

Fatty Acids

The omega-3 fatty acids contained in the cranberry seed oil extracts of the invention are essential for growth and development throughout the life cycle. For example, omega-3 fatty acids are known to play an important role in, 1) the normal function of the retina and brain, especially in new born infants, 2) maintaining favorable serum triglycerides in normal subjects and in patients with hypertriglyceridemia, 3) the normal function of the vascular and neurological systems, and 4) reducing LDL (low density lipoprotein) cholesterol in patients with hyperlipidemia (provided that the saturated fatty acid content in the diet is decreased).

In normolipidemic subjects, omega-3 fatty acids can prevent and rapidly reverse the carbohydrate-induced hypertriglyceridemia, decrease platelet aggregation, lower blood viscosity, decrease fibrinogen levels, lower tendency for thrombus formation, inhibit production of platelet-derived growth factor (PDGF), increase endothelium-derived relaxing factor (EDRF), and inhibit production of platelet activating factor (PAF). Moreover, the omega-3 fatty acids can also function as an anti-inflammatory and reduce joint pain in patients with rheumatoid arthritis. Still further, omega-3 fatty acids have been linked to a role in gene expression, benefiting patients with ulcerative colitis, decreasing the toxicity of cyclosporin in patents with psoriasis, and improving skin lesions.

Similarly, the omega-6 (linoleic acid) and omega-9 (oleic acid) fatty acids, also derivable from cranberry seed oil extracts of the invention, play important roles in normal physiological functions. In addition, these fatty acids have also been associated with various health benefits relating to overall growth, healthy skin, reproduction, and cardiovascular health.

Accordingly, formulations can be prepared by those of ordinary skill in the art containing one or a combination of the above-mentioned desirable fatty acids. Such formulations have application in the medical and pharmaceutical industries for enhancing, maintaining or treating any of the above-mentioned biological functions or disfunctions. In addition, given the wide spectrum of biologic processes affected by these fatty acids, the cranberry seed oil extract of the invention can also be used as a food additive or dietary supplement.

For example, in the food industry, to raise the availability of desirable fatty acids in a consumer's diet, the cranberry seed oil extract of the invention, or compositions derived therefrom (e.g., containing components or fractions thereof), can be added to, for example, juices, bakery products, infant formulas, etc. As dietary supplements, the cranberry seed oil extract of the invention or compositions derived therefrom can be taken in the form of e.g., liquids, pills, or capsules as are known in the art. As discussed further below, methods for formulating such vehicles of administration can be performed using standard techniques.

In another embodiment, the cranberry seed oil extract of the invention or compositions derived therefrom (e.g., containing health-promoting fatty acids) can be fed or otherwise administered to laying hens to produce eggs rich in desirable fatty acids, or to cows or other livestock to produce meat and dairy products rich in such fatty acids. The resultant food products derived from these animals can then be consumed by humans for their enhanced nutritional and health benefits.

Alternatively, the cranberry seed oil extract of the invention or compositions derived therefrom can be fed or otherwise administered to animals, such as pets or domesticated livestock, for therapeutic purposes (e.g., to correct problems such as dry skin, allergic reactions, and cancer).

II. Minor Components

Cranberry seed oil extracts of the invention also contain a number of minor components having significant therapeutic value.

Sterols

In particular, cranberry seed oil extracts of the invention can contain one or more sterols, including, but not limited to, βsitosterol (Δ-5) and schottenol (Δ-7) (also referred to as stigmastenol).

Plant sterols (phytosterols) have been shown to inhibit the absorption of cholesterol absorption from the intestine, and decrease blood serum cholesterol. It has been proposed that, in the intestine, phytosterols act by reducing the solubility of cholesterol in the lipid and micellar phases with a consequential decrease in cholesterol absorption. Plant sterols are also reported to inhibit colon cancer development.

Accordingly, the cranberry seed oil extracts of the invention and compositions derived therefrom (e.g., fractions rich in phytosterols) can be used, for example, in the treatment of patients with hypercholesterolemia or as chemopreventative agents against colon cancer.

Triterpene Alcohols

In addition, cranberry seed oil extracts of the invention also can contain one or more triterpene alcohols. As part of the present invention, several triterpene alcohols were identified including, but not limited to, β-amyrin, α-amyrin, and 24-methylene parkeol, the three primary alcohols. Such triterpene alcohols are known to confer significant health benefits, e.g., against heart disease and cancer, due to their strong antioxidant properties.

Accordingly, cranberry seed oil extracts of the invention and compositions derived therefrom (e.g., fractions rich in triterpene alcohols) can be used to treat diseases including, but not limited to heart disease and cancer.

Phenolic Compounds

Cranberry seed oil extracts of the invention also can contain one or more (e.g., at least two) phenolic compounds, such as methoxyphenylpropionic acid and methoxycinnamic acid.

Such phenolic compounds can act as potent antioxidants and, therefore, can prevent or delay oxidation reactions which cause various diseases. Accordingly, the cranberry seed oil extracts of the invention and compositions derived therefrom can be used as used as anti-oxidants. For example, they can inhibit lipid peroxidation, scavenge free radicals and active oxygen, inactivate lipoxygenase, and chelate iron ions. They also can be used to inhibit erythrocyte aggregation and sedimentation. Moreover, epidemiological studies have demonstrated that the consumption of phenolic compounds is associated with a reduced risk of cancer. Accordingly, the cranberry seed oil extract of the invention and compositions derived therefrom (e.g., fractions rich in phenolic compounds) can be used to treat cancer with fewer side effects compared to standard chemotherapies.

Tocochromanols (Tocopherols and Tocotrienols)

Cranberry seed oil extracts of the invention also contain a remarkably high concentration of tocochromanots (a class of compounds that includes tocopherols and tocotrienols), such as α-tocopherol, γ-tocopherol, δ-tocopherol, α-tocotrienol, γ-tocotrienol, δ-tocotrienol, or a combination thereof. A large body of research has shown the importance of tocopherols and tocotrienols in the defense against numerous biological disorders. To date, palm oil is the only other edible oil known to contain tocotrienols in a significant amount, however, isolated cranberry seed oil of the invention has two major advantages over palm oil. First, cranberry seed oil extracts of the invention contain a much higher concentration of the beneficial γ-tocotrienol (about 1,600 mg/kg) as compared to palm oil (400 mg/kg). Second, cranberry seed oil extracts of the invention have the superior advantage over palm oil of having very little of the undesirable palmitic acid (only 6% vs. 46%), the saturated fatty acid thought to contribute to heart disease.

Accordingly, cranberry seed oil extracts of the invention and compositions derived therefrom (e.g., fractions rich in tocochromanols) can be used to treat respiratory, inflammatory, neurological, dermatological, opthalmological, and gastroenterological diseases. Surprisingly, the amount of tocotrienols determined to be in the cranberry seed oil extract of the invention (a total of more than 1,700 mg/Kg) exceeds that in any other oil known so far. In particular, cranberry seed oil is remarkably rich (~1,500 mg/Kg) in γ-tocotrienol which has been shown to be, in most cases, the more biologically active of the tocotrienol isomers. In contrast, palm oil has a total tocotrienol content only of approximately 500–700 mg/Kg, with far less of the desirable γ-T3 (only 280–400 mg/Kg compared to cranberry seed oil which has approximately 1,500 mg/Kg). Other food oils, for example, barley, rice, and rice bran oils and brewers grain, contain in the range of 400–700 mg/Kg γ-T3. However, their importance as edible oils is negligible in view of the very small amounts that can be economically extracted from the grains. In addition, several of these grains contain oil susceptible to enzymatic hydrolysis, e.g., rice bran oil. All other known edible oils are extremely poor in γ-T3. Finally, the cranberry seed oil extracts of the invention also have a pleasing flavor and aroma.

Tocochromanols—Structure, Nomenclature, and Prevalence

Figure 11:
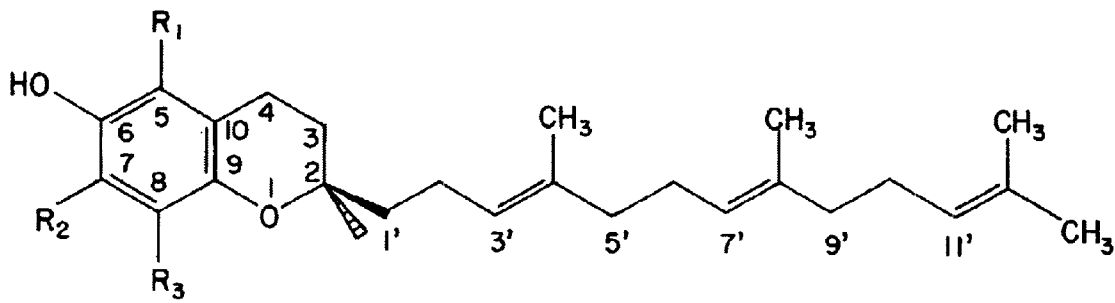
FIG. 11 shows the chemical structure of the α-, β-, γ-, δ-tocotrienol (top panel) and the chemical structure of α-, β-, γ-, δ-tocopherol (bottom panel).
Figure 11:
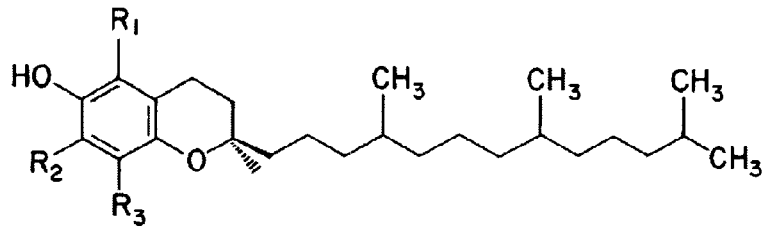

The tocochromanols include the major active components of vitamin E and are capable of alleviating vitamin E deficiency symptoms. The tocochromanols include the tocopherols (T) and the tocotrienols (T3). All have derivatives which differ according to the position and number of methyl groups present on the chromanol ring and are designated as the α, β, γ, and δ-isomers. The side chains consist of three isoprenoid units which, in the case of the tocopherols (FIG. 1, bottom), are completely saturated while the tocotrienols have double bonds at positions 3', 7', and 11' (FIG. 11, top).

Distribution and Sources of Tocotrienols

In general, tocopherols predominate in oil seeds and green parts of higher plants, whereas the tocotrienols predominate in the aleurone and subaleurone layers of cereal seeds (especially rice bran oil and barley oil) and in palm oil. The distribution of tocopherols and tocotrienols in some common oils (Table 2) and their distribution in cereals and brans (Table 3) is provided below. Prior to the instant invention, palm oil was the most practical source of tocotrienols.

TABLE 2

Approximate Content of Tocopherol and Tocotrienol Found in Vegetable Oils (mg/kg)

|  | Tocopherols | | | | Tocotrienols | | | |
| --- | --- | --- | --- | --- | --- | --- | --- | --- |
|  | α-T | β-T | γ-T | δ-T | α-T$_3$ | β-T$_3$ | γ-T$_3$ | δ-T$_3$ |
| Coconut | 5–10 | — | 5 | 5 | 5 | Trace | 1–20 | — |
| Cottonseed | 40–560 | — | 270–410 | 0 | — | — | — | — |
| Maize, grain | 60–260 | 0 | 400–900 | 1–50 | — | 0 | 0–240 | 0 |
| Maize, germ | 300–430 | 1–20 | 450–790 | 5–60 | — | — | — | — |
| Olive | 1–240 | 0 | 0 | 0 | — | — | — | — |
| Palm | 180–260 | Trace | 320 | 70 | 120–150 | 20–40 | 260–300 | 70 |
| Peanut | 80–330 | — | 130–590 | 10–20 | — | — | — | — |
| Rapeseed/canola | 180–280 | — | 380–590 | 10–20 | — | — | — | — |
| Safflower | 340–350 | — | 70–190 | 230–240 | — | — | — | — |
| Soybean | 30–120 | 0–20 | 250–930 | 50–450 | 0 | 0 | 0 | — |
| Sunflower | 350–700 | — | 10–50 | 1–10 | — | — | — | — |
| Walnut | 560 | 20–40 | 590 | 450 | — | — | — | — |
| Wheat germ | 560–1200 | 660–810 | 260 | 270 | 20–90 | 80–190 | — | — |

TABLE 3

Tocopherols and Tocotrienols in Different Cereals and Brans

| Cereals and their brans | Tocopherols (ppm) | | | | Tocotrienols (ppm) | | | |
| --- | --- | --- | --- | --- | --- | --- | --- | --- |
|  | α-T | β-T | γ-T | δ-T | α-T$_3$ | β-T$_3$ | γ-T$_3$ | δ-T$_3$ |
| Wheat | 14 | 7 | 0 | 0 | 33 | 0 | 0 | 0 |
| Wheat germ | 239 | 90 | 0 | 0 | 30 | 100 | 0 | 0 |
| Wheat bran | 16 | 10 | 0 | 0 | 13 | 55 | 0 | 0 |
| Corn | 6 | 0 | 45 | 0 | 3 | 0 | 5 | 0 |
| Oat | 5 | 1 | 0 | 0 | 11 | 2 | 0 | 0 |
| Rye | 16 | 4 | 0 | 0 | 15 | 8 | 0 | 0 |
| Rice, white | 1 | 0 | 1 | 0 | 1 | 0 | 2 | 0 |
| Rice, brown | 6 | 1 | 1 | 0 | 4 | 0 | 10 | 0 |
| Rice, bran | 6 | 1 | 0 | 8 | 1 | 4 | 4 | 6 |
| Rice, bran | 3 | 15 | 4 | 2 | 1 | 14 | 22 | 29 |
| Barley | 2 | 4 | 0 | 1 | 11 | 3 | 2 | 0 |
| Barley bran | 11 | 16 | 36 | 4 | 36 | 25 | 19 | 11 |
| Brewers grain | 31 | 42 | 114 | 20 | 199 | 40 | 39 | 34 |

Diet, Vitamin E, and Cancer

It has been shown that increasing fat-derived energy in the diet, and increasing the linoleic acid content of diets at constant fat-derived energy, results in increased tumorigenicity (Birt et al., *J. Clin.*, 45:203–209 (1987), Birt et al., *Nutr. Rev.*, 48:1–(1990); Carroll et al., *Current Opinion in Lipidology*, 8:53–56 (1997); Erickson et al., *Nutr. Rev.*, 48:6–14 (1990); Ip et al., *Cancer Res.*, 45:1997–2001 (1985); Ip et al., *Am. J. Clin. Nutr.*, 45:218–224 (1987); Thompson et al., *Cancer Res.*, 49:1904–1908 (1989); Welsch et al., *Am. J. Clin. Nutr.*, 45:192–303 (1987)). The effect of linoleic acid is thought to occur via its influence on prostanoid metabolism, immune response, or cell membrane structure and function. Increasing the fat-derived energy content of diets of equal linoleic acid content by the addition of palm oil did not enhance tumorigenesis in moderately exercised rats (Thompson et al., *Cancer Res.*, 49:1904–1908 (1989)). Results reported by Sundram, et al. (*Cancer Res.*, 49:1447–1451, (1989)) suggest that crude palm oil is more effective than refined, bleached, and deodorized palm oil in increasing the latency (the interval between administration of a carcinogen and appearance of a palpable tumor) of 7,12-dimethybenz(a)anthracene (DMBA)-initiated tumorigenesis.

The use of vitamin E as an anticarcinogenic agent has been recognized for a number of years (Haenszel et al., *Int. J. Cancer*, 36:43–48 (1985); Menkes et al., N. Engl. J. Med., 315:1250–1204 (1986); Stahelin et al., *Ann. NY Acad. Sci.*, 570:391–399 (1989)). In addition, in vitro and in vivo studies, including human studies, have demonstrated that vitamin E interferes with the development of carcinogenesis that results from exposure to various environmental factors known to enhance oxidant stress (Borek et al., In, *Mechanisms of cellular transformation by carcinogenic agents*, New York, Pergamon (1987), Borek et al., In, *Medical, biochemical and chemical aspects of free radicals*, Amsterdam, Elsevier, (1989); Borek et al., *Proc. Natl. Acad. Sci. USA* 83:1490–1494 (1986); *Proc. Natl. Acad Sci. USA*, 88:1953–1957 (1991)). In addition, α-tocopherol, a component of vitamin E, is a hydrophobic, peroxyl radical trapping, chain-breaking antioxidant found in biological membranes. Accordingly, the protective role vitamin E plays in inhibiting a variety of human malignancies is mainly attributed to its components having the ability to protect the lipid material of the organs against oxidation (Ames et al., *Science* 230:271–279 (1987); Doll et al., *J. Natl. Cancer Inst.* 66:1193–1194 (1981): Greenwald et al., *Cancer* 65:1483–1490 (1990); Menzel et al., *J. Agr. Food Chem.*, 20:481–486 (1972)).

Methods for Evaluating Therapeutic Properties of Cranberry Seed Oil Extract and Components Derived Therefrom In Vivo Animal and Clinical Studies In one embodiment, cranberry seed oil extracts of the invention and compositions derived therefrom can be tested for their therapeutic effect by administering (e.g., orally or by injection) the extracts or compositions in a suitable form (e.g., as a pharmaceutical composition or dietary supplement) to a human or other animal, and then observing the physiological effect (e.g., compared to a control). The human or animal can, for example, be suffering from a disease or condition, such as those described herein (e.g., cancer, hypercholesterolemia or heart disease). Thus, a reduction in the physical symptoms of the disease can be measured as an indication of the therapeutic efficacy of the cranberry seed oil extract or compositions derived therefrom.

Cell Proliferation Assays

The health promoting properties of cranberry seed oil extracts of the invention and compositions derived therefrom also can be evaluated using a variety of art-recognized cell proliferation assays. Suitable methods include, for example, those described below.

To evaluate anti-tumor activity, cranberry seed oil extracts of the invention or compositions derived therefrom (e.g., a fraction thereof) can be used in a controlled animal study. In general, tumors are induced in the animal via diet, by applying chemical tumor promoter to the skin, or by the implantation of tumor cells in the presence or absence of the test agent. Various assays, such as those described below, can then be used to examine the progress of carcinogenesis in the presence or absence of the administration of the extracts or compositions of the invention.

In one embodiment, a tumor cell proliferation assay is performed by measuring the incorporation of [$^3$H] thymidine into the DNA of dividing cells, as is known in the art. For example, a solution containing a cranberry seed oil extract of the invention or components derived therefrom (e.g., a tocopherol or tocotrienol rich fraction) can be added to tissue culture plates, for example, in decreasing concentrations and incubated at 37° C. for 3 days, after which tritiated thymidine is added to each well to determine the number of dividing cells at each concentration. The cells are further incubated for a sufficient period of time, e.g., 4 hrs, to allow for the incorporation of the radiolabel into the DNA of dividing cells and then medium and excess label are removed. The cells can then be harvested by, e.g., trypsinization, and the amount of radioactivity present in the cells is measured using standard techniques. The concentration at which the extracts of the invention exhibit 50% inhibition of cell growth (IC50) is determined by comparing the radioactivity measured in the extract-treated cells as compared to the untreated control cells.

Viability Assays

To assess the viability of tumor cells after exposure to a cranberry seed oil extract of the invention or a composition derived therefrom, the cells can be mixed with 3-[4-5-dimethylthiazol-2-yl)-2,5-diphenyl-tetrazolium bromide (MTT). The intensity of the blue color, due to a formazan product formed by cellular reduction of MTT by the mitochondrial dehydrogenase of the surviving cells, is then measured as an indication of the viability of the remaining cells (Hansen et al., *J. Immunol. Methods*, 119:203–210 (1989)). Percent viability can be determined by relating absorbance/concentration of the treated cells to that of the non-treated controls.

Long Term Growth Assays

The long term growth effects on cells caused by exposure to a cranberry seed oil extract of the invention or a composition derived therefrom can be determined by incubating plates containing the cell culture medium plus the reagent at its IC50 concentration at 37° C. Plates are removed at appropriate intervals, the medium aspirated, the cells trypsinized, resuspended, counted with a hemocytometer, and the number of cells plotted against time to construct growth curves.

Methods of Use

Treatment of Cancer

In one embodiment, a cranberry seed oil extract of the invention and compositions derived therefrom (particularly those having high tocotrienol content) can be administered to a human or other animal to treat or prevent a variety of cancers. The extract and compositions derived therefrom also can be administered in combination with other anti-cancer agents. In particular, the cranberry seed oil extracts of the invention and compositions derived therefrom can be administered with either tamoxifen and/or a flavonoid for the treatment of, for example, breast cancer. These combinations of agents encompassed by the invention are particularly effective because of the ability of tocotrienols to act in synergy with tamoxifen and/or flavonoids in the inhibition of tumorigenic cells.

For example, it is known that most breast cancers consist of hormone-dependent as well as hormone independent cells. The drug tamoxifen, a synthetic non-steroidal estrogen antagonist, has been widely used in the treatment of hormone-responsive breast cancer. In addition, the inhibitory effects of various combinations of the palm oil tocotrienol-rich fractions as well as individual tocotrienols in combination with tamoxifen on at least two breast cancer cell lines (i.e., estrogen receptor-negative MDA-MB-435 and estrogen receptor-positive MCF-7) have been demonstrated (see Table 4) (Guthrie, et al., *Asia Pacific J. Clin. Nutr.* 41–45 (1997)).

TABLE 4

Inhibition of Proliferation of MDA-MB-435 and MCF-7 by Combinations of Tocotrienols with Tamoxifen

| Inhibitor | MDA-MB-435 IC$_{50}$, µg/mL | MCF-7 IC$_{50}$, µg/mL |
| --- | --- | --- |
| α-Tocopherol | >1000 | 125 ± 3 |
| TRF | 180 ± 3 | 4 ± 0.1 |
| α-Tocotrienol | 90 ± 3 | 6 ± 0.3 |
| γ-Tocotrienol | 30 ± 2 | 2 ± 0.1 |
| δ-Tocotrienol | 90 ± 3 | 2 ± 0.05 |
| Tamoxifen | 90 ± 4 | 0.04 ± 0.001 |
| α-Tocopherol + Tamoxifen | 46.9 ± 2 | |
| TRF + Tamoxifen | 3.9 ± 0.2 | 0.5 ± 0.02 |
| α-Tocotrienol + Tamoxifen | 1.5 ± 0.05 | 0.1 ± 0.005 |
| γ-Tocotrienol + Tamoxifen | 1.9 ± 0.02 | 0.01 ± 0.0002 |
| δ-Tocotrienol + Tamoxifen | 5.9 ± 0.1 | 0.003 ± 0.0001 |

In particular, it was concluded with regard to MDA-MB-435 cells, that gamma-tocotrienol was a much more effective inhibitor of proliferation than tamoxifen alone. However, when TRF, α-tocopherol, α-, γ- or δ-tocotrienols were combined in equimolar concentration with tamoxifen, the combinations inhibited cell proliferative much more effectively than when used alone. Importantly, these studies showed that most cells were viable at the IC$_{50}$ concentration at which compounds were added suggesting that the anti-tumor compounds are not toxic when administered at therapeutically effective dosages. A synergistic effect was also evident when these combinations of compounds were tested on cell growth over a longer period of time.

With regard to studies performed using MCF-7 breast cancer cells, tocotrienol-rich fractions were shown to inhibit the proliferation of MCF-7 cells more effectively than α-tocopherol, but not as effectively as tamoxifen. In addition, the tocotrienols gave much lower IC$_{50}$ in MCF-7 cells than in MDA-MB-435 cells with γ-T$_3$ and δ-T$_3$ being the most effective. In most cases, however, the compounds used in combination with tamoxifen (1:1) showed IC$_{50}$ values intermediate between those of the individual compounds used alone. Only γ-T$_3$ and δ-T3 gave lower IC$_{50}$ values when combined with tamoxifen than when used alone, with the δ-T3/tamoxifen combination being remarkably potent. Similar inhibitory effects of these combinations were observed on cell viability and growth.

Prior to the present invention, treatment of cancer patients with tamoxifen had several drawbacks. For example, tumors can develop resistance to tamoxifen, possibly caused by the drug's intrinsic estrogen antagonist properties (Osborne et al., *J. Natl. Cancer Inst.* 87:746–750 (1995)). Also, tamoxifen may increase the incidence of new primary malignancies, e.g. endometrial, liver, and colorectal cancers (Rutgrist et al., 1995). Accordingly, the present invention provides the advantage of enabling the administration of tamoxifen in lower doses, for example, in combination with a cranberry seed oil extract of the invention or a composition derived therefrom (particularly one having a high tocotrienol content) to avoid these undesirable effects.

Synergy With Flavonoids

In another embodiment, a cranberry seed oil extract of the invention or a composition derived therefrom is administered in combination with tamoxifen as described above and/or in combination with a flavonoid for the treatment or prevention of cancer. These combinations of agents encompassed by the invention are particularly effective because of their known ability to act in synergy, as demonstrated below, in the inhibition of tumorigenic cells.

Flavonoids are polyphenolic compounds which occur in plant foods, particularly citrus. These compounds include the flavones, e.g. tangeretin; the flavavones, e.g. hesperetin; the isoflavones, e.g. genistein; and the flavonols, e.g. quercetin. Several studies have demonstrated the anticancer properties of flavonoids from various plant sources (Cook et al., *J. Nutr. Biochem.* 7:66–76 (1996); Hertog et al., *Nutr. Cancer* 20:21–29 (1993); Middeleton et al., *Trends Pharm. Sci.*, 5:335–338 (1984)). Further, various combinations of flavonoids from different sources have been shown to be synergistic in their ability to inhibit the proliferation of a breast cancer cell line (MDA-MB-435 cells).

In particular, synergistic effects between the tocotrienols and flavonoids, with $\gamma$-$T_3$ and tangeretin being the most effective combination, have been observed when tested for their ability to inhibit growth in MDA-MB-435 and MCF-7 breast cancer cells ($IC_{50}$ 0.05 $\mu$g/mL and 0.02 $\mu$g/mL, respectively) (Guthrie et al., *Asia Pacific J. Clin. Nutr.* 6:41–45 (1997)). In addition, with few exceptions, combinations (1:1:1) of tocotrienols, flavonoids, and tamoxifen were more effective than 1:1 combinations of $T_3$ and flavonoids, $T_3$ and tamoxifen, or flavonoids and tamoxifen and these are summarized in Table 5, below. The most potent combinations were $\gamma$-$T_3$/tangeretin/tamoxifen with the MDA-MB-435 cells ($IC_{50}$ 0.01 $\mu$g/mL), and $\delta$-$T_3$/hesperetin/tamoxifen ($IC_{50}$ 0.0005 $\mu$g/mL) with the MCF-7 cells.

Accordingly, cranberry seed oil extracts of the invention and compositions derived therefrom (particularly those having high tocotrienol content) can be used in combination with tamoxifen and/or flavonoids as potent anti-cancer agents.

TABLE 5

Synergy of Tocotrienols with Tamoxifen and Flavonoids in the Inhibition of Proliferation

|  | MDA-MB-435 | MCF-7 MCF |
| --- | --- | --- |
| $\gamma$-$T_3$ only | 30 | 2 |
| Tangeretin only | 0.5 | 0.4 |
| Tamoxifen only | 90 | 0.04 |
| $\gamma$-$T_3$ + tangeretin | 0.5 | 0.02 |
| $\gamma$-$T_3$ + tamoxifen | 2 | 0.01 |
| Tangeretin + tamoxifen | 0.5 | 0.08 |
| $\gamma$-$T_3$ + tangeretin + tamoxifen | 0.01 | 0.02 |
| $\delta$-$T_3$ + Hesperetin + tamoxifen | 6 | 0.0005 |

Tocotrienols in the Treatment of Heart Disease

In another embodiment, cranberry seed oil extracts of the invention and compositions derived therefrom (particularly those having high tocotrienol content) can be used to treat or prevent heart disease. Indeed, the efficacy of various tocotrienols in reducing cholesterol levels in animals, including humans, is well supported in the scientific literature.

Animal studies have shown that tocotrienol-containing bran oil, barley oil, and palm oil suppressed cholesterologenesis when fed to chicken. In particular, corn oil plus a palm oil-tocotrienol-rich fraction (TRF) which contained 15–20% $\alpha$-T, 12–15% $\alpha$-$T_3$, 35–40% $\gamma$-$T_3$, and 25–30% $\delta$-T3, affected a significant reduction in total serum cholesterol, i.e., from 170 mg/dl to 106 mg/dl. Purified $\gamma$ and $\delta$-tocotrienols were also noted to be more potently hypocholesterolemic than $\alpha$-tocopherol, TRF, or $\alpha$-tocotrienol, when fed to hypercholesterolemic chicken. Hypercholesterolemic pigs fed the TRF-supplemented diet showed a 44% decrease in total serum cholesterol and a 60% decrease in LDL cholesterol, with the decrease persisting for 8 weeks even after putting the animals back on the control corn-based diet (Quereshi et al., In, *International Palm Oil Conference*, pp 45–47 (1988)).

Moreover, a study involving 47 hypercholesterolemic subjects administered dietary supplements containing 200 mg of TRF per day for 4 weeks resulted in, respectively, a 15–22% and 10–20% reduction in serum total and LDL cholesterol (Quereshi, et al., *Lipids* 20:817–824 (1985); Quereshi, et al., *Am. J. Clin. Nutr.*, 53:1021S–1026S (1991)). In addition, in studies where the hypocholesterolemic effect of tocotrienols was compared with that of other drugs, the tocotrienols were more effective. For example, in a study involving chickens, T3 was demonstrated as being twice as effective as Lovastatin™, a drug currently used for cholesterol control in humans. And most of the drugs most commonly used today in the therapy of hypercholesterolemia (i.e., Nicotinic acid (Grundy et al., *J. Lipid Res.*, 22:24–36 (1981)), Compactin™ and Lovastatin™ (Illingworth et al., *Eur. Heart J., Supp.* E:103–111 (1987); Endo et al., *Biotechnology*, 26:301–320 (1994)), Cholestyramine™ and Colestipol™ (Shepherd et al., *Biochem. Soc. Trans.* 15:199–201 (1980)), Clofibrate™ and Gemfibrosil™ (Kesaniemi et al., *JAMA*, 251:2241–2246 (1984)) and Probucol™ are known to produce various side effects (Illingworth et al., *Am. J. Cardiol.*, 60:33G–42G (1987)). In contrast, no toxic effects were observed in the studies where tocotrienols were administered.

Accordingly, cranberry seed oil extracts of the invention and compositions derived therefrom (particularly those having high tocotrienol content) can be used in the treatment of heart disease.

Tocotrienols in the Treatment of Other Diseases and Disorders

In yet another embodiment, cranberry seed oil extracts of the invention and compositions derived therefrom (particularly those having high tocotrienol content) can be used in the treatment or prevention of a wide range of other diseases and disorders that include aging, respiratory, inflammatory, neurological, dermatological, opthalmological, and gastroenterological diseases. Indeed, a large volume of reported research provides evidence that vitamin E-containing tocochromanols plays a critical role in the above-mentioned conditions.

In addition, as presented herein, the tocotrienols, which are also members of the vitamin E family, have proved in many cases to be even more protective than $\alpha$-tocopherol. Accordingly, cranberry seed oil extracts of the invention and compositions derived therefrom having both of these active compounds (i.e., tocopherols and tocotrienols) are especially well suited for the treatment of a broad spectrum of biological conditions linked to the action of tocopherols and/or tocotrienols. Moreover, such extracts and compositions of the invention also are well suited to the treatment of any yet to be characterized biological disorders or diseases that, at some level, are affected by or controlled by a mechanism linked to the action of, a tocopherol or tocotrienol.

For example, cranberry seed oil extracts of the invention and compositions derived therefrom can be used to prevent endothelial injury, such as ischemic and reperfused myocardium and ulcers. In addition, the extracts and compositions can be used to inhibit tumor necrosis factor biosynthesis which, in turn, decreases inflammation (e.g., by inhibiting respiratory bursts of neutrophils or via free radical scavenging). Accordingly, cranberry seed oil extracts of the invention and compositions derived therefrom (particularly those having high tocopherol and/or tocotrienol content) can be used as antiinflammatory agents for the prevention and treatment of a wide variety of diseases and conditions involving minor, acute and chronic inflammation. These include, but are not limited to, fever, rheumatoid diseases, pain, functio laesa, hypertension and edema.

Cranberry seed oil extracts of the invention and compositions derived therefrom (particularly those having high tocochromanol (e.g., tocotrienol) content) also can be used to treat glucose intolerance in diabetes mellitus, and/or to restore acute glucose-induced insulin response in non-insulin-dependent diabetes mellitus. In addition to their role in inflammatory response, prostaglandins have also been shown to inhibit glucose-induced insulin release, increase glucose concentration and stimulate glucagon secretion. Consequently, use of the compounds of the invention can lead to an increased insulin to glucagon ratio.

In addition to the above-stated uses, cranberry seed oil extracts of the invention and compositions derived therefrom (particularly those having high tocotrienol content) can be used to enhance the immune response in animals and humans, for example, by reducing the amount of fatty acids in biological tissues. Since fatty acid levels effect the immune system, the compounds of this invention may serve as immunoregulators. They may, for example, be used to increase antibody titers to foreign proteins.

In addition, the reduction in fatty acid, cholesterol, fatty acid and/or glucose levels induced by the compounds of the invention can be obtained without attendant substantial weight loss, resulting in an increased feed to protein conversion ratio. Therefore, the extracts and compositions of the invention can be used to increase feed conversion efficiency.

Hypercholesterolemic diseases and conditions that can be treated using the cranberry seed oil extracts of the invention and compositions derived therefrom include, but are not limited to, atherosclerosis, arteriosclerosis, xanthomatosis, hyperlipoproteinemias, and familial hypercholesterolemia.

Thrombotic diseases and conditions that may be treated using cranberry seed oil extracts of the invention and compositions derived therefrom include, but are not limited to, pulmonary disease (for example, involving reduced conductance, compliance, or constriction), excessive fluid accumulation or pulmonary edema, respiratory distress, asthma, pulmonary vascular permeability, pulmonary vasoconstriction, pulmonary hypertension, pulmonary embolism, cardiac ischemia, myocardial infarction, cardiopulmonary bypass associated dysfunction, vasoconstriction, organ dysfunction, platelet dysfunction, cardiac disease, chronic obstructive arterial disease caused by arteriosclerosis, vasoconstriction, renal artery stenosis, myocardial infarction, stroke, deep vein thrombosis, peripheral arterial occlusion, and other blood system thromboses.

The antioxidizing properties of the cranberry seed oil extracts of the invention and compositions derived therefrom may also be applied to, but are not limited to, the treating and preventing of cancerous conditions by, for example, preventing or limiting cancer-causing mutations in the genetic material of an animal or a human.

Antiatherogenic diseases and conditions that can be treated using cranberry seed oil extracts of the invention and compositions derived therefrom include, but are not limited to, atherosclerosis, arteriosclerosis, myocardial infarction, ischemia (i.e., myocardial ischemia, brain ischemia, and renal ischemia) and strokes.

Inflammatory diseases and conditions that can be treated using cranberry seed oil extracts of the invention and compositions derived therefrom include, but are not limited to, essential hypertension, hypertension of congestive heart failure, renal dysfunction caused by reduced myocardia output, endotoxemia, chronic liver disease or hypertension, pulmonary inflammation in asthma, lung injury (bronchitis, pneumonia, or acute); rheumatic diseases (for example, rheumatoid arthritis or systemic lupus erythematosus), inflammatory bowel disease (for example, ulcerative colitis), irritable bowel disease (such as villous adenoma), gastrointestinal disorders caused by excess acids, pepsin or bile salts, Zollinger-Ellison syndrome, skin diseases or trauma (such as burns or acid or caustic injury), gout, Bartter's syndrome, fever, rheumatoid diseases, pain, and functio laesa.

Immunoregulatory diseases and diseases that can be treated using cranberry seed oil extracts of the invention and compositions derived therefrom include, but are not limited to, autoimmune diseases, for example, AIDS, chronic fatigue syndrome, graft rejections, and other viral diseases that impair the immune system.

Formulations and Methods of Administration

Cranberry seed oil extracts of the invention and compositions derived therefrom can be administered to a subject in any suitable form. For example, the extracts and compositions of the invention are sufficiently stable such that they can be readily prepared in a form suitable for adding to various foodstuffs including, for example, juice, fruit drinks, carbonated beverages, breakfast cereals, biscuits, cakes, muffins, cookies, toppings, bread, bagels, fiber bars, soups, crackers, baby formulae, salad dressings, cooking oils, and meat extenders.

In addition, cranberry seed oil extracts of the invention and compositions derived therefrom can be formulated as a pharmaceutical composition (e.g., a medicinal drug) for the treatment of specific disorders.

In another embodiment, cranberry seed oil extracts of the invention and compositions derived therefrom can be formulated as a dietary supplement.

Suitable additives, carriers and methods for preparing such formulations are well known in the art.

For example, pharmaceutical compositions may take the form of tablets, capsules, emulsions, suspensions and powders for oral administration, sterile solutions or emulsions for parenteral administration, sterile solutions for intravenous administration and gels, lotions and cremes for topical application. The pharmaceutical compositions may be administered to humans and animals in a safe and pharmaceutically effective amount to elicit any of the desired results indicated for the compounds and mixtures described herein. In addition, the extracts of the invention may be used in cosmetics.

The pharmaceutical compositions of this invention typically comprise a pharmaceutically effective amount of a cranberry seed oil extract or fraction thereof containing, for example, a tocochromanol-containing cranberry seed oil extract, and if suitable a pharmaceutically acceptable carrier. Such carriers may be solid or liquid, such as, for example, cornstarch, lactose, sucrose, olive oil, or sesame oil. If a solid carrier is used, the dosage forms may be tablets, capsules or lozenges. Liquid dosage forms include soft gelatin capsules, syrup or liquid suspension.

Therapeutic and prophylactic methods of this invention comprise the step of treating patients or animals in a pharmaceutically acceptable manner with the compositions and mixtures described herein. As used herein, the term "pharmaceutically effective amount" refers to an amount effective to achieve a desired therapeutic effect, such as lowering blood levels of LDL-cholesterol and total serum cholesterol, while increasing the ratio of HDL-cholesterol to LDL-cholesterol, inhibiting lipogenesis, inhibiting platelet aggregation, decreasing the release of superoxides by human peripheral blood neutrophils, reducing levels of tumor necrosis factor or interleukin-1, reducing levels of arachadonic acid, increasing antibody titers in the blood, preventing thrombosis, preventing or treating inflammatory diseases, immunoregulatory diseases, fever, edema, diabetes mellitus, cancer, signs of aging, pain, septic shock, chronic fatigue syndrome and functio laesa; or decreasing the concentration of lipoproteins in the blood or to increase feed conversion efficiency.

The pharmaceutical compositions of this invention may be employed in a conventional manner for the treatment and prevention of any of the aforementioned diseases and conditions. Such methods of treatment and prophylaxis are well-recognized in the art and may be chosen by those of ordinary skill in the art from the available methods and techniques. Generally, dosage ranges may be from about 1 to about 1000 mg/day. However, lower or higher dosages may be employed. The specific dosage and treatment regimens selected will depend upon factors such as the patient's or animal's health, and the severity and course of the patient's (or animal's) condition and the judgment of the treating physician.

The cranberry seed oil extracts of the invention and compositions derived therefrom also can be used in combination with conventional therapeutics used in the treatment or prophylaxis of any of the aforementioned diseases. Such combination therapies advantageously utilize lower dosages of those conventional therapeutics, thus avoiding possible toxicity incurred when those agents are used alone. For example, tocotrienols or tocotrienol-like compounds of the invention may be used in combination with bile acid sequestrants, such as Cholestyramine™ and Colestipol™; fibric acid derivatives, such as, Clofibrate™, Gamfibrozil™, Bezafibrate™, Fenofibrate™, and Ciprofibrate™; HMGR inhibitors, such as Lovastatin™, Mevastatin™, Pravastatin™, Simvastatinm™ and SRI-62320; Probucol™; Nicotinic Acid (e.g., derivatives and conjugates), or estrogen antagonists, such as, for example, tamoxifen.

In foodstuffs, the cranberry seed oil extracts of the invention and compositions derived therefrom can be used with any suitable carrier or edible additive. For example, the cranberry seed oil extracts of the invention may be used as cooking oil, frying oil, or salad oil and may be used in any oil-based food, such as margarine, mayonnaise, or peanut butter. In addition, grain flour fortified with the compounds of the invention may be used in foodstuffs, such as baked goods (for example, breads, muffins, and pastries), cereals, pastas and soups. The cranberry seed oil extracts of the invention and compositions derived therefrom also can be emulsified and used in a variety of water-based foodstuffs, such as drinks, for example, juice drinks, sports drinks, and drink mixes. Advantageously, the above-mentioned foodstuffs may be included in low fat, low cholesterol, or otherwise restricted dietary regimens.

Pharmaceutical compositions, dietary supplements, and foodstuffs of the present invention can be administered to humans and animals such as, for example, livestock and poultry. Once an animal has consumed or otherwise been administered the composition, it can advantageously retain the hypercholesterolemic, antithrombotic, antioxidizing, antiinflammatory, antiatherogenic, immunoregulatory, and other advantageous biological activities of the administered compounds. Accordingly, an animal raised under these conditions, or any product derived therefrom, such as, for example, milk, may be consumed by a human or another animal to derive the benefits of the cranberry seed oil extracts of the invention or compositions derived therefrom. For example, a chicken which ingests feed fortified with the extracts of the invention may later be eaten by a human to derive the cholesterol-reducing benefits.

In addition, the administration of the cranberry seed oil extracts of the invention or a composition derived therefrom can result in an increase in feed conversion efficiency. For example, in higher fat content animals, such as cattle, swine, sheep, and lamb, the tocotrienol containing cranberry seed oil extracts can advantageously lead to faster growth, lower cholesterol content, and higher percentage lean meat. When the compounds of the invention are administered to poultry, the tocotrienol containing cranberry seed oil extract can result in the production of eggs characterized by a reduced cholesterol content of the yolk and a higher protein content of the egg white.

Methods for Extracting Cranberry Seed Oil

The novel extracts of the invention may be isolated from cranberry seeds using any suitable method, such the solvent system described in the examples provided below.

In a preferred embodiment, the invention provides an extraction method for isolating cranberry seed oil by physically disrupting the cranberry seeds, adding to the seeds an organic solvent to produce an extract/solvent mixture, and removing the solvent portion of the extract/solvent mixture such that an isolated cranberry seed oil substantially free of solvent results. In one embodiment of the extraction method, an isolated cranberry seed oil results that is suitable for use in a foodstuff, dietary supplement, or pharmaceutical composition. Other non-solvent based methods of extraction, such as cold pressing, can also be used.

Methods for Isolating and Analyzing Specific Components from Cranberry Seed Oil

To isolate and analyze constituent components of cranberry seed oil, a variety of art-recognized techniques and assays can be employed. For example, as described in the studies provided herein, cranberry seed oil samples can be prepared for analysis by converting the fatty acids in the oil to their methyl esters, for example, by refluxing with MeOH/MeO$^-$Na$^+$. The resultant methyl esters can then be analyzed, e.g., by gas chromatography.

Sterol and triterpene alcohols can be extracted and analyzed using, for example, thin layer chromatography and high-performance liquid chromatography. For example, the isolated cranberry seed oil can be saponified with KOH, the unsaponifiables extracted with ether, and the resultant material can be fractionated on thin-layer chromatography (TLC)

plates where the individual bands that are subsequently resolved can be scraped and extracted with a chloroform/methanol solvent. These resultant samples can then be analyzed using, e.g., gas and high-performance liquid chromatography (HPLC).

Phenolic compounds of cranberry seed oil can be analyzed and extracted using HPLC analysis and solvent extraction, respectively. The isolated oil can be dissolved in hexane and then extracted with a methanol/water solution followed by centrifugation. The extract can then be dried, and the residue can be resuspended in methanol/water for HPLC analysis.

Tocochromanols contained in the cranberry seed oil of the invention can be separated and analyzed using, for example, the methods of Carpenter (Carpenter, Jr., A. P., *J. Amer. Oil Chemists' Soc.*, 56:668 (1979)).

Other methods known in the art may also be employed, in place of or in combination with, the methods described above for isolating cranberry seed oil components, particularly to "scale up" the quantity of the isolated components. For example, chromatographic techniques may be used for isolating either major or minor components of the cranberry seed oil of the invention, in sufficient and pure quantities, such that the component may be administered alone or as part of a composition or product described herein (e.g., foodstuffs, dietary supplements, pharmaceuticals, etc.). In particular, gas liquid chromatography, gas solid chromatography, high pressure or high performance liquid chromatography (HPLC) (e.g, normal, reverse, or chiral), ion exchange chromatography, or size exclusion chromatography can be employed as described, for example, in *Advances in Chromatography*, Brown, Eds., Marcel Dekker, Pub. (1998); *Basic Gas Chromatography*, Harold et al., John Wiley & Sons, Pub. 1997); *Column Handbook for Size Exclusion Chromatography*, Wu, Ed., Academic Press, Pub. (1999); *Fundamentals of Preparative and Nonlinear Chromatography*, Guichon et al., Eds., Academic Press, Pub. (1994); *Handbook of Process Chromatography: A Guide to Optimization, Scale-Up and Validation*, Hagel et al., Eds., Academic Press, Pub. (1997); *HPLC Methods for Pharmaceutical Analysis*, Lunn et al., John Wiley & Sons, Pub. (1997); and *Practical High-Performance Liquid Chromatography*, Meyer, Wiley-Liss, Pub. (1999), each of which is incorporated by reference herein. Such isolated components, which can be separated as "value added" fractions (e.g., fractions having therapeutic value), are typically rich in at least one selected major or minor component of the cranberry seed oil of the invention. These isolated components or fractions may be further combined to provide a composition rich in more than one component, including major components, minor components, and combinations thereof. In addition, a particular formulation intended for the treatment or prevention of a particular disease or condition may be formulated to be rich in those components having a therapeutic effect on the disease or condition (e.g., associated with affecting a change in any of the mechanisms associated with that particular disease or condition). For example, a formulation suitable for administering to a subject with cancer is preferably rich in cranberry seed components having antioxidant and other anti-cancer properties, whereas a formulation for administering to a subject with a dietary need, may be rich in, for example, beneficial fatty acids.

Methods for Inhibiting Oxidation and Increasing Stability

In addition to the general precautions taken during the extraction process to avoid any unnecessary exposure to oxygen, e.g., protective blanketing of the extracts with carbon dioxide or nitrogen gas, the extracts and compositions derived therefrom of the invention may be further preserved by, for example, exposing the extracts to BHT, ascorbic acid, low temperature, or a combination of these conditions.

This invention is further illustrated by the following examples which should not be construed as limiting. The contents of all references, patents and published patent applications cited throughout this application are incorporated herein by reference.

EXAMPLE 1

Method of Extracting Cranberry Seed Oil (Small Scale)

In this example, a method for performing small scale extractions of oil from cranberry seeds is described.

This extraction method is useful for extracting sufficient amounts of cranberry seed oil, for example, for performing laboratory analyses of its components. Accordingly, the extraction method described herein allowed for the identification and characterization of each class of relevant components present in cranberry seed oil (see Example 3). The novel method is carried out as follows (see FIG. 1).

First, cranberry seeds are flaked without prior hull removal. This is in contrast to other oil seeds, which are usually dehulled first and then broken into grits that are in turn flaked. However, cranberry seeds are too small to conveniently submit to this procedure. The flaking step results in the disruption of each seed hull causing partial extrusion or expulsion of the seed meat which allows for efficient oil extraction. Ideally, proper flaking produces flaked seeds having a speckled appearance due to the contrast between the yellow partly expelled seed meat and the outer red hull. It has been observed that improperly flaked seeds that are not speckled, i.e. are primarily red in appearance, do not extract as well as speckled seeds. Typically, the flaking step is carried out at room temperature rather than at higher temperatures (e.g., about 80° C.) as is usually done with other oil seed grits. In addition, to protect the seed oil from unnecessary exposure to oxygen, the flaker is blanketed with an inert gas (nitrogen).

Next, cranberry seeds are mixed with dry ice prior to their being ground in a hammer mill in preparation for batch extraction. The use of dry ice creates a blanket of nitrogen which prevents overheating of milled material in choked sections of the hammer mill and greatly reduces the flow of oxygen-containing air through the mill and the ground seeds it contains. Cool, inert-gas blanketed flaking provides material that is extracted more readily, offer less flow resistance, and flows more uniformly through the mill and, thus, is superior to methods that involve grinding of the seeds.

Figure 2:
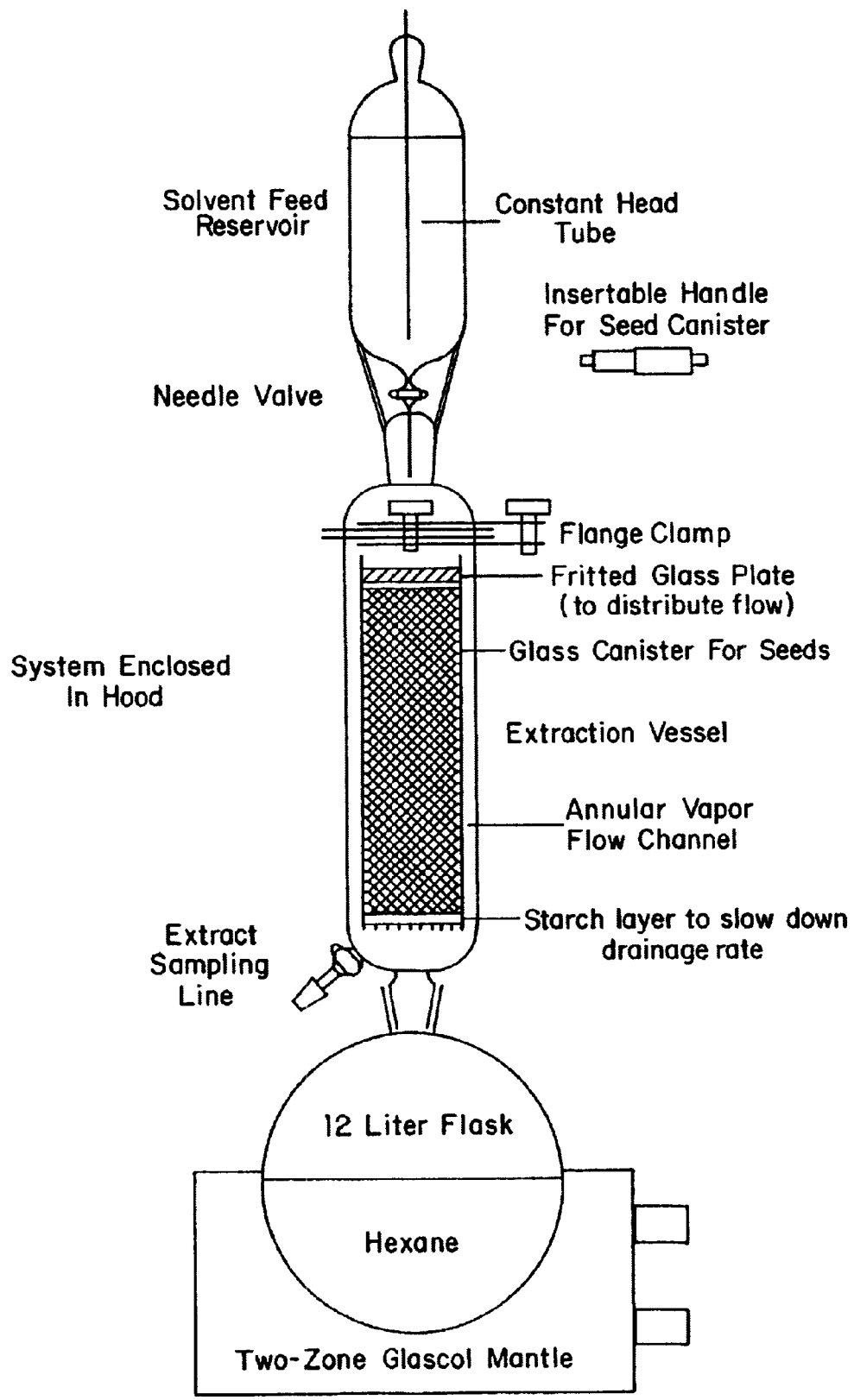
FIG. 2 shows a detailed diagram of an apparatus for solvent extraction of cranberry seed oil from cranberry seeds.

After mechanical disruption of the cranberry seeds, the flakes were then exposed to the solvent hexane using the apparatus diagramed in FIG. 2. Typically, ground seeds were loaded into canisters to form a bed about 35 cm deep. A layer of corn starch was added as an inert material to assist in achieving an ideal flow rate of solvent through the seed material. Approximately six liters (4,152 grams) of hexane was used and allowed to percolate through the seed material at the flow rates indicated in tabular form below.

The final step of the method liberates isolated cranberry seed oil of a sufficient amount and quality for laboratory analysis (see Example 3). The solvent may be removed using standard techniques. The oil concentrations from each run (as shown in Table 6) were calculated from density measurements conducted using a pycnometer.

TABLE 6

Summary of Small Scale Extraction Data

| Run No. | Load in grams | Solvent in grams | Extract in grams | Time (hrs) | Flow Rate cc/min | Liquid Velocity cm/min | Conc. @ 100% Yield |
|---|---|---|---|---|---|---|---|
| 1 | 1476 | 4152 | 3014 E + 160 D | 3 | 35 | 0.3 | 10.3% |
| 2 | 1449 | 2974 E 160 D 506 H | 2878 | ~4.7 | 19 | 0.16 | 21.4% |
| 3 | 1539 | 4152 H | 2825 E + 199 D | 3.5 | 28.5 | 0.24 | 6.9% |
| 4 | 1775 | 2974 E 142 D 1262 H | 3233 E + 96 D | 2.75 | 36.3 | 0.31 | 15.1% |

EXAMPLE 2

Method of Extracting Cranberry Seed Oil (Large Scale)

In this example, a method for performing a large scale extraction of oil from cranberry seeds is described.

Figure 3:
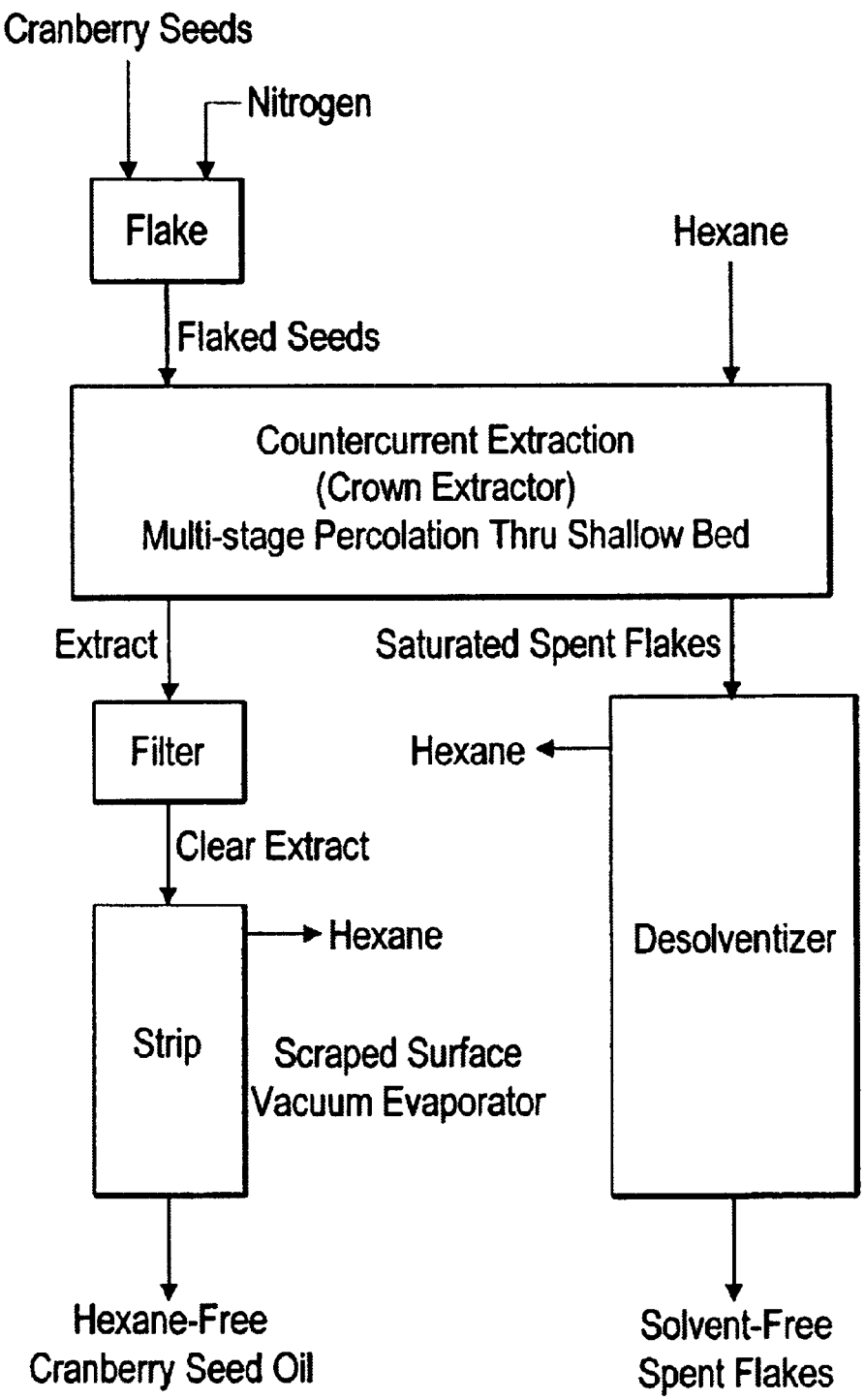
FIG. 3 shows a flow chart for extracting cranberry seed oil from cranberry seeds. The method shown is particularly suitable for large scale production of cranberry seed oil.

This extraction method is useful for extracting sufficient amounts of high quality cranberry seed oil for commercial applications (e.g. as food additives, dietary supplements, pharmaceuticals, cosmetics, etc.). A flowchart depicting an overview of the large scale extraction process is provided in FIG. 3. The extraction method is described in detail under the following subsections, below.

Apparatus

The large extraction apparatus (diagrammed in FIG. 3) consists of flaking and conditioning equipment, extractor, desolventizer, condenser, solvent and recovered solvent storage tanks, and a two-effect, steam-heated, tube-based, rising-film evaporator and associated condenser. In addition, the large scale apparatus also comprises a small, scraped-surface, vacuum evaporator (Luwa evaporator) with roughly 4 ft$^2$ of heat-transfer surface and an associated condenser cooled by refrigerated water.

Flaking

Figure 4:
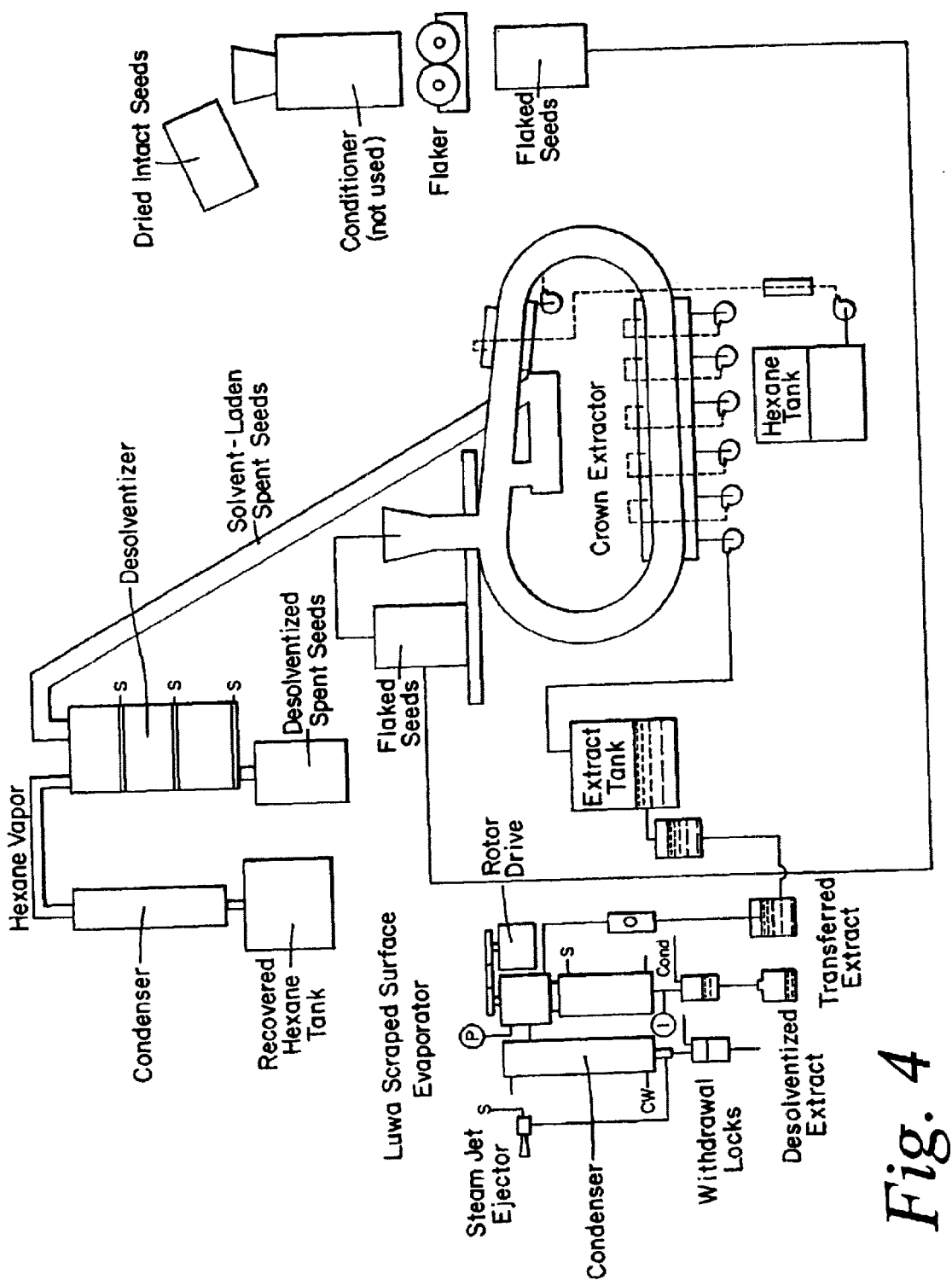
FIG. 4 shows a schematic of a physical plant for large scale cranberry seed oil production using a Crown extractor.
Figure 5:
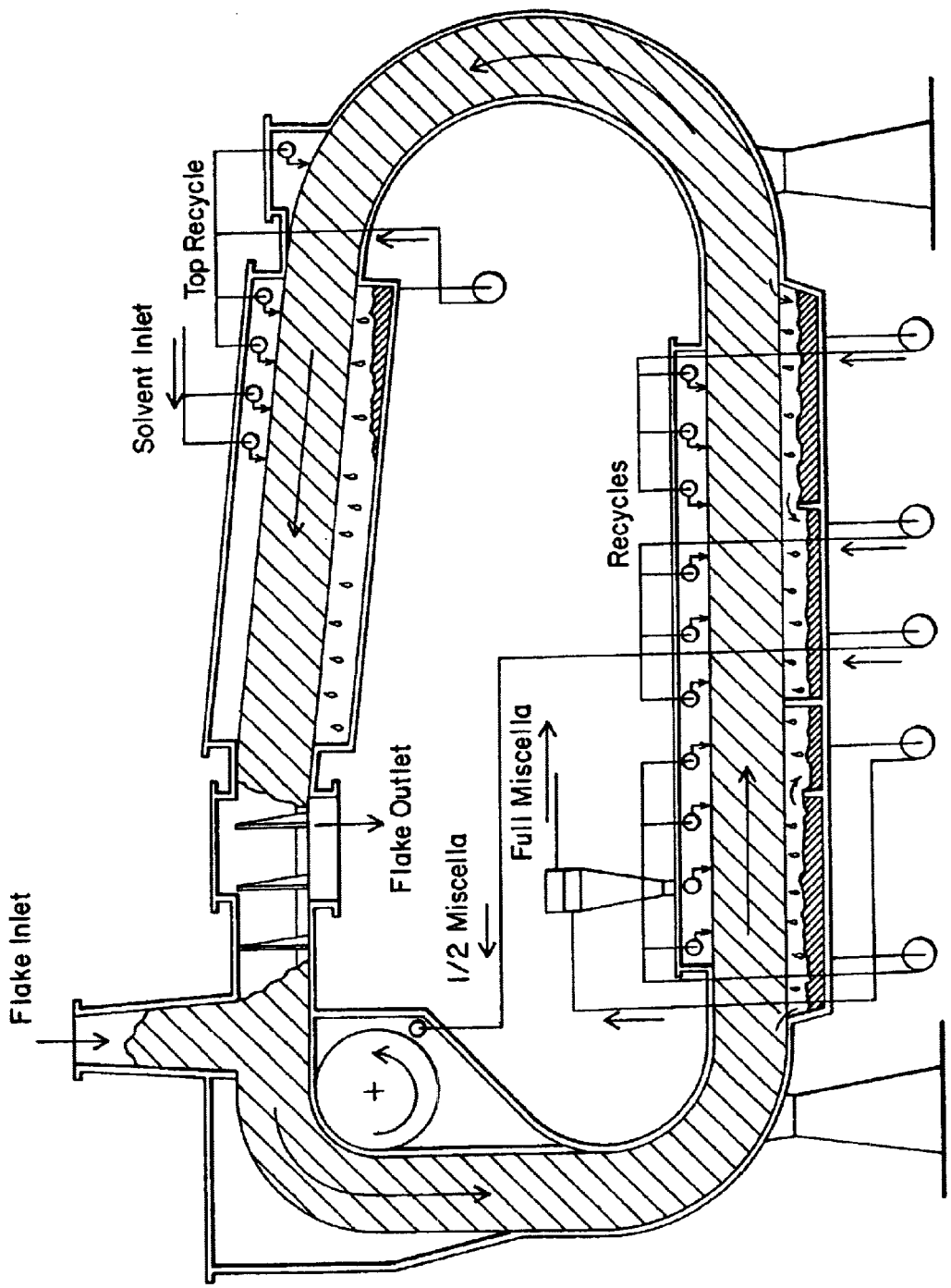
FIG. 5 shows a detailed diagram of a Crown extractor.

An amount of 800 lbs. of dried cranberry seeds were processed in the pilot plant depicted in FIG. 4. Appropriate amounts of cranberry seeds were manually fed into the feed hopper of the Crown extractor. Periodically, proper flaking was monitored using under a small portable microscope. Acceptable flaking is characterized by seeds with clearly split hulls from which a great deal of light colored yellowish material has extruded. Because of such extrusion, well-flaked seeds appear speckled with well intermingled small patches of red and light yellow. Poorly flaked seeds appear redder and contain mostly intact hulls.

Flaking was carried out under nitrogen which flowed into a housing covering the top of the flaking rolls. The rolls are roughly 18-inches in diameter and roughly 2-ft wide, counter-rotate, and osculate at a narrow nip. Pressure at the nip is adjusted by using a heavy screw to adjust the degree of compression of heavy springs pressing against shaft bearings of one of the rolls.

Extraction

In contrast to conventional protocols which involve operating oil extractors at slightly below the normal boiling point of hexane (69° C.), the method of the invention used an extractor that was operated at or near room temperature. Specifically, hexane temperatures in the extraction system ranged between 80 and 88° F. at the start of the run and rose to 90 to 95° F. near the end of the extraction run. Low temperature extraction was used because it is gentler and still provides both good extraction yield and rapid extraction. In addition, in order for the low-temperature extraction to be safely used, void space in the extractor was filled with an inert gas to prevent flammable or explosive vapor-air mixtures from forming. The low temperature extraction and minimization of exposure to oxygen reduced damage to oxidation-sensitive components of the oil, and prevents polymerization and gelling of the oil. Because cranberry seed oil has a high level of polyunsaturated acids it can readily act like a polymerizable drying oil. Gelling or partial polymerization would make recovery of trace ingredients from the oil much more difficult.

It is noted that much lower evaporation temperatures can be used if less stringent hexane removal is employed. Only moderate hexane removal is required if the extracted oil is going to be subsequently processed to recover the minor constituents. The oil should be immediately cooled by passing it through a chilled heat exchanger as it leaves the evaporator. Since holdup times in scraped-surface evaporators are very short, a few seconds at most, the time of exposure of the oil to heat can be greatly reduced.

Cranberry seed flakes entered the extractor through a hopper near the right hand end of the top leg, were dragged into and through the system by the drag bars on the chain-link drive, descended through a vertical leg and entered the bottom leg where they moved from left to right, contacting progressively leaner and leaner extract. The flakes were then dragged upward through a vertical leg and were contacted by very lean extract and fresh solvent. Flakes were then passed over a drainage section where part of the interstitial extract in the bed discharged. The drained flakes were then dropped out of the extractor into an inclined drag conveyor which carried the flakes upward and deposited them in the top of the desolventizer, whose operation is described later. The vertical, descending bed of flakes at the left-hand side of the extractor prevents hexane vapor escaping from the extractor. Sight glasses were used in the extract application and drainage zones to monitor deposition and drainage of hexane from the flake bed. The particular extractor used in carrying out this method was seven feet long and 0.627-feet wide and typically allowed for a five-inch deep bed of flakes to be processed.

Under the above conditions, 157 lbs. of cranberry seed flakes per hour and 180 lbs. of extract per hour were fed into the extractor. The resultant extract/solid ratio ((E/R)=1.15) was slightly higher than the ratio normally used (E/R=0.8 to 1.0) for oil seeds in Crown extractors. Using these processing rates, a total of 625 lbs. of flakes were fed into the extractor and 425 pounds of desolventized flakes were discharged from the desolventizer. Fifty gallons of extract were produced. Based on a single sample whose density was 0.74 grams/cm$^3$, and using a density versus concentration equation we developed (and correcting for small temperature effects) the extract concentration was determined to be about 24%. Accordingly, given the following calculation 50 gallons×8.34×0.74 lbs./gallon=308.6 lbs. of extract collected 308.6 lbs.×0.24 (% concentration)=74 lbs. of oil we determined that 74 lbs. of high quality cranberry seed oil were produced using the above method. This corresponds to a nominal yield of 11.8% (74 lbs. of oil/625 lbs. of flakes× 100%=11.8%).

Extraction Yield Improvements

Abnormal operating conditions are used when starting up and shutting down a large extractor. Yield losses due to the need to accumulate material in the extractor during startup and due to material left in the extractor at shutdown cause nominal yields for short runs to be much lower than yields for steady-state operation. Accordingly, differences between the nominal yield for a short run and that for steady-state operation depend on the start-up and shut-down conditions used. Based on the occupied chain length, bed depth, width and bulk density, the extractor was estimated to contain 131 lbs. of flakes. In addition, solvent flow was not started until flakes reached the solvent inlet port (top, right-hand side) of the extractor. Thus, based on an estimate of the amount of extract held up in the system, it is more likely that extract discharge starts 55 minutes after solids feeding begins. This estimate suggests that no yield would be obtained during the 55 minutes of feeding, and the net amount of flakes fully subject to extraction during the run would only be 494 lbs. (625 lbs. of total flakes−131 lbs. of flakes held up in the system=494 lbs. of flakes actively processed). Accordingly, using the method of the invention with the above considerations in mind, it is estimated that the yield obtainable from a steady-state operation would be as great as 74/494×100%= 15.0%. This corresponds to a yield of 15.0/21.5×100%= 69.7% based on an initial oil content of 21.5% for cranberry seeds.

Evaporation

The extract processed above was then evaporated to be substantially free of solvent under a vacuum and using no added heat. Alternatively, the extract can be processed as above by heating to 60° C. (140° F.) by using heating coils in the extract receiver (the receiver is normally maintained under a vacuum of 7–8 in. of H$_2$O). When this is done, a great deal of solvent evaporates in the receiver, and the residual solvent can be readily evaporated in the Luwa evaporator (a scraped-surface, vacuum evaporator). Further, the extract can also be sent to a two-effect, tubular, rising-film evaporator (operating at slightly higher vacuum than the Luwa) where most of the solvent can be removed at operating temperatures close to that used in the Luwa. This partly desolventized extract can then be sent to the Luwa evaporator to remove even more hexane. Holdup times in the tubular evaporator are relatively long whereas those in the Luwa evaporator are quite short, only a few seconds.

A preferred evaporation method for gentler and shorter holdup times at high temperature employed the use of the Luwa evaporator without preheating the extract in the extract receiver. The Luwa evaporator was operated at a vacuum of 22 inches of Hg maintained using a steam jet ejector. In the evaporator, a rapidly rotating wiper acted on the extract as it flowed down the inner wall of a steam-heated tube. This provided very good heat transfer and minimized resistance of hexane transfer across the oil film. Though high steam temperatures were used, fluid temperatures in the upper part of the evaporator were about 32° C., the boiling point of hexane in a vacuum of 22-in. of Hg. As the extract fluid flowed down the tube, sufficient hexane evaporated to reduce its mole fraction in the extract to about 0.5, a weight fraction of about 90% and the fluid temperature was calculated as rising to about 50° C. If hexane still behaved fairly ideally when its concentration dropped to 4.5%, the fluid temperature would have risen to about 70° C.

Hexane exhibits large negative deviations from ideality at low concentrations. Based on curves developed with cottonseed oil extraction, 220° F. (105° C.) of heat is needed to provide 2% residual hexane in cottonseed oil. Accordingly, steam pressure and the extract inflow rate were set to achieve a 220° F. outlet temperature for oil leaving the evaporator. Hexane driven off from extract in the evaporator passed over into condenser cooled with refrigerated (10° C.) water. Non-condensables and any hexane that did not condense, passed out of the system through the steam condenser used to maintain vacuum.

Product

A total of 36 lbs. of stripped oil (i.e., substantially free of solvent) were collected having a density of 0.92 gr/cm$^3$ at 80° F. (27° C.). This corresponds to roughly 0.926 grams/ cm$^3$ at 20° C. Based on a concentration versus density formula, this corresponds to 79% oil (based on a pure oil density of 0.995 gr/cm3). Most vegetable oils have densities in the 0.915 to 0.94 gram/cm$^3$ range, and the listed density for, e.g., pure linseed oil, ranges from 0.92 to 0.94 gram/ cm$^3$.

Flake Recovery

The flakes were desolventized by successively passing them as a four or five-inch deep bed over three, steam-heated, circular trays in the desolventizer. The bed of flakes was slowly swept around the trays by rotating rakes and after a complete circuit on one tray fell through a choked opening in the tray onto the tray below. Trays were heated with 120 psig steam (350° F.–177° C.) and the solvent driven off in the desolventizer was condensed and recovered. A total of 425 lbs. of desolventized flakes were recovered with another 25 lbs. of flakes estimated to be hung up in niches in the equipment. Accordingly, it was determined that the 625 lbs. of seed flakes lost roughly (625−450)=175 lbs. of weight or 175/625×100%=28% of their original weight in the extraction process. This exceeds the estimated extraction yield of 15% for continuous extraction by 13%. The extra loss in weight is estimated to be largely due to evaporation or loss of moisture from the seeds during extraction and desolventization.

It is noted that the appearance of spent flakes discharged from the desolventizer changed during the course of the run. Initially, flakes were speckled and contained like amounts of white spots. Later they were redder and appeared to contain more intact seeds. This is an indication that flaking efficiency can decline during extraction and should be monitored in order to avoid suboptimal yields. Another variable which can lead to suboptimal yields is high bed permeability. A high bed permeability can reduce the amount of time flakes are in contact with solvent/extract. A simple equation can be used in carrying out the method of the invention. If A/R represents the amount of solvent absorbed or entrained per unit mass of flakes and if E/R/A/R−1<1, the fractional yield based on initial oil content can never be greater than E/R/A/R−1. In the present case, a relatively low E/R was used to obtain an oil-rich extract and reduce the amount of solvent that had to be removed in the Luwa extractor. Preferably, this aspect of the invention can be manipulated and a yield approaching 100% can be achieved by using a high enough E/R. To achieve such results, the A/R can be measured such that an appropriate E/R is set.

Conditioner

In carrying out the above described method of the invention, seeds fed to the flaking rolls were not exposed to heat. However, it is understood that a modification of the invention could also include heating the seeds (e.g., to a temperature of 170° F. or 180° F.) in a conditioner (a device containing swept, steam heated trays) prior to flaking. This step can inactivate lipase and make the seeds easier to flake.

EXAMPLE 3

Analysis of the Components of Cranberry Seed Oil

In this example, cranberry seed, isolated using the methods of the invention described above, was subjected to a detailed analysis of its major and minor components. Accordingly, a detailed description of the major and minor components of cranberry seed oil is described in the following subsections.

Major Components

Fatty Acid Composition

An analysis of the fatty acid composition of cranberry seed oil (CSO) was performed by converting an cranberry seed oil sample to its methyl esters by refluxing with MeOH/MeO$^-$Na$^+$ followed by refluxing with MeOH/HCl. The methyl esters were then analyzed by gas chromatography using a Supelcowax 10 column (size, 30 m; i.d.,0.32 mm; film thickness, 0.25 mm). The carrier gas employed was Helium, the oven temperature and injection port temperature was 250° C., FID 260° C., and the program used was 1 min at 180° C., 180–220° C. at 10°/min, 4 min at 220° C. The results of this analysis are provided below in Table 7.

TABLE 7

Fatty Acid Composition of Cranberry Seed Oil
Composition moles %

| Fatty Acid | 1 | 2 | 3 | 4 | Average |
|---|---|---|---|---|---|
| 16:0 | 6.7 | 6.55 | 6.4 | 6.5 | 6.5 |
| 18:0 | 1.1 | 1.1 | 1.3 | 1.2 | 1.2 |
| 18:1 | 21.1 | 21.2 | 21.2 | 21.2 | 21.2 |
| 18:2 | 38.05 | 38.0 | 38.1 | 37.8 | 38.0 |
| 18:3 | 33.05 | 33.15 | 33.1 | 33.2 | 33.1 |

The above results demonstrate that cranberry seed oil is unique in its high content of both linoleic acid (omega-6) and α-linolenic acid (omega-3) fatty acids.

In order to further characterize the fatty acid distribution in the isolated cranberry seed oil, the triglyceride composition in the oil was analyzed according to the triglyceride carbon number using gas chromatography. The column characteristics were as follows: DBI, L=4.5 m; film: 0.1 um; i.d.=0.317; injection, on column; and gas; Helium at 40 Kpa. The temperature program used was as follows:

180° C. 1 min, 180° C. ↑280° C. ↑340° C. 5° C./min, 340° C. 2 min FID=37° C.

Analyses according to ECN (ECN=Number of carbon atoms less 2 for each double bond present; glycerol carbon atoms not included in the count), is given Tables 8 and 9, below.

TABLE 8

Analysis of Fatty acids in Cranberry Seed Oil According to their ECN Numbers

| NAME | CONC | RT | AREA | RF |
|---|---|---|---|---|
| ECN36 | 4.658 | 8.54 | 2443311 | 1.000 |
| ECN38 | 12.330 | 10.44 | 6467236 | 1.000 |
| ECN40 | 21.837 | 12.99 | 11453112 | 1.000 |
| ECN40 | 2.734 | 15.07 | 1434129 | 1.000 |
| ECN40 | 21.124 | 17.29 | 11079193 | 1.000 |
| ECN42 | 5.793 | 19.17 | 3038255 | 1.000 |
| ECN44 | 8.185 | 22.46 | 4293041 | 1.000 |
| ECN44 | 5.646 | 23.80 | 2961219 | 1.000 |
| ECN44 | 3.489 | 24.86 | 1830110 | 1.000 |
| ECN44 | 3.516 | 26.27 | 1843976 | 1.000 |
| ECN46 | 5.124 | 31.02 | 2687546 | 1.000 |
| ECN46 | 3.073 | 34.31 | 1611877 | 1.000 |
| ECN46 | 0.263 | 36.02 | 137941 | 1.000 |
| ECN48 | 1.213 | 43.46 | 636120 | 1.000 |
| ECN48 | 1.015 | 47.80 | 532182 | 1.033 |
| 16 | 0.000 | 65.94 | 102807 | |
| TOTALS | 100.000 | | 52552055 | |
| UNNORMALIZED TOTAL 5244924800.000 | | | | |

TABLE 9

Summary of ECN Analysis

| NAME | CONC |
|---|---|
| ECN36 | 4.658 |
| ECN38 | 12.330 |
| ECN40 | 24.571 |
| ECN42 | 26.916 |
| ECN44 | 20.836 |
| ECN46 | 8.460 |
| ECN48 | 2.227 |
| TOTAL | 100.00 |

Stereo-Chemical Analysis

A further characterization of the fatty acids in cranberry seed oil was performed using stereo-chemical analysis. The analysis was conducted on a silica column using a purified sample in anhydrous ether and subsequently reacted with EtMgBr for 30 sec to obtain a limited decomposition (Table 10. Verification was done by thin-layer chromatography (TLC) using a hexane-ether solvent mix (50:50, v/v), which permitted the separation of the sn-1,2 and the sn-23 diglycerides.

Calculation of the internal ($A_i$) and external ($A_e$) positions is conducted according to the following relationships.

$$A_i = 4 A_{DG\alpha\beta}^{31\ 3A} t$$

$$A_e = 3A_t - A_i/2$$

where:

At=A in total glycerides

Ai=A in internal positions $A_{DG\alpha\beta}^{31\ 3A} t$=A in the 1, 2 and 2, 3 positions Ac=A in external positions Results of the Stereo-Chemical Analysis are summarized in Table 10, below.

TABLE 10

|  | C16:0 | C18:0 | C18:1 | C18:2 | C18:3 |
|---|---|---|---|---|---|
| % Mol. | 6.5 | 1.2 | 21.2 | 38.0 | 33.1 |
| $A_i$ (β) | 5.0 (25.5) | 1.3 (33.4) | 23.4 (36.7) | 44.0 (38.5) | 26.3 (26.4) |
| $A_e$ | 7.2 (74.5) | 1.0 (66.6) | 20.1 (63.3) | 35.1 (61.5) | 36.5 (73.6) |

It is clear from the above data that the fatty acids of cranberry seed oil, have a beta-position is rich in oleic (omega-9), linoleic (omega-6), and linolenic (omega-3) acids—a unique phenomenon in view of the stereoselectivity of the human pancreatic lipase. Cranberry seed oil can thus be considered a potentially valuable source for application in medical research.

Analysis of Minor Components

Analysis of the Sterols and Triterpene Alcohols

In order to determine the particular sterol and alcohol content present in cranberry seed oil (see Table 11), the following protocol was used. An oil sample extracted according to the methods above was saponified using KOH and the unsaponifiable fraction was extracted with ether and fractionated on thin layer chromatographic plates coated with silica. The developing solvent consisted of anhydrous hexane/ether/formic acid (S0:50:1, v/v/v). The bands corresponding to sterols, 4α-methyl sterols, and triterpene alcohols were scraped and extracted at ambient temperature with anhydrous $HCCl_3$/MeOH (90:10, v/v). Qualitative and quantitative analysis of each class was carried out via gas chromatography, high performance liquid chromatography (HPLC), nuclear magnetic resonance (NMR), and mass spectrometry (MS). The amounts of the different classes were determined to be as listed below.

| (a) Total Unsaponifiables in the oil | 2.6% |
|---|---|
| (b) Total Triterpenic compounds: | |
| in the unsaponifiables | 51.4% |
| in the oil | 1.3% |
| (c) Sterols in the unsaponifiables | 30.7 |
| in the oil | 7982 mg.Kg$^{-1}$ |
| in the triterpenic fraction | 87.8% of which 60% were Δ5 and 27.8% were Δ7 sterols |
| (d) Triterpene Alcohols | |
| in the unsaponifiables | 6.7% (or 1742 mg.Kg$^{-1}$) |
| in the triterpenic fraction | 12.2% |

The presence of 4α-methylsterols was at very low concentrations and therefore not quantifiable by HPLC.

Further analytical detail was obtained for each class of components above.

Analysis of the Sterols

Cranberry seed oil was determined to contain several sterols (see Table 11) of which two were present in relatively large amounts (relative gas chromatographic retention times of 1.33 and 1.45 were noted). The mass spectra analysis of both sterols showed identical molecular ions at m/z 414 with the empirical formula $C_{29}H_{50}O$). However, NMR spectroscopy indicated that one of the sterols had the intracyclic double bond at position 5 (i.e., Δ5) while the other sterol had a double bond at position 7 (i.e., Δ7).

Accordingly, the major MS features of the Δ5 sterol were:
414 (M$^+$, 82%), 396 (M-H$_2$O, 93%), 381 (M-H$_2$O-Me, 44%), 329 (M-H$_2$O—C$_5$H$_7$, 13%) 303 (M-H$_2$O—C$_9$H$_{10}$, 31%), 273 (M-C$_{10}$H$_{21}$, 45%) 255 (273-H$_2$O, 70%), 231 (273-C$_3$H$_6$—H, 49%), 213 (231-H$_2$O, 100%).

And the major MS features of the Δ7 sterol were:
414 (M$^+$, 75%), 399 (M-Me, 37%), 381 (M-Me-H$_2$O, 14%), 273 (M-C$_{10}$H$_{21}$, 31%), 255 (273-H$_2$O, 100%), 231 (273-C$_3$H$_5$—H, 34%), 213 (231-H$_2$O, 58%).

Figure 6:
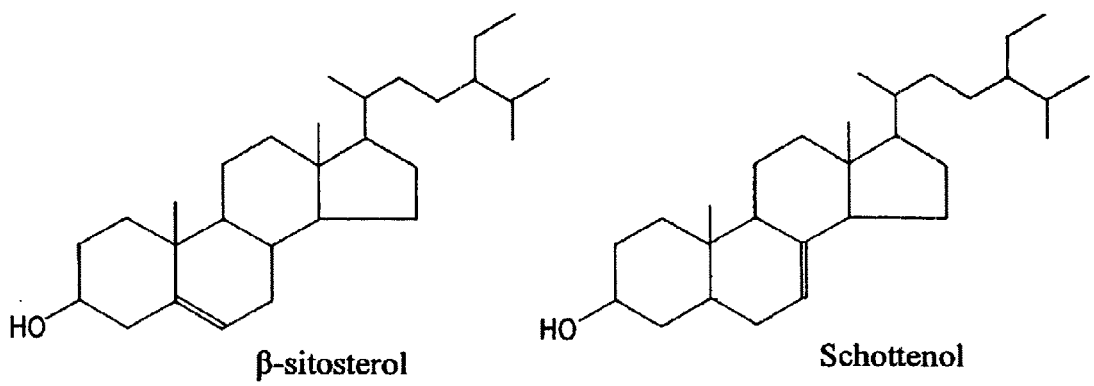
FIG. 6 shows the chemical structure of two major sterols in cranberry seed oil, β-sitosterol and schottenol (i.e., stigmastenol).

Based on the above data, the Δ5 sterol was confirmed to be β-sitosterol (80.1%), and the Δ7 sterol was determined to be schottenol (i.e., stigmastenol) (19.9%) as shown in FIG. 6.

TABLE 11

ANALYSIS OF THE STEROLS IN CRANBERRY SEED OIL

| STEROL | % |
|---|---|
| COLESTEROL | 0.08 |
| 24 METYLENCOLESTEROL | 0.03 |
| CAMPESTEROL | 3.87 |
| CAMPESTANOL | 0.22 |
| STIGMASTEROL | 1.37 |
| Δ7 CAMPESTEROL | 1.19 |
| (NK) | 1.37 |
| Δ5-23 STIGMASTADIENOL | 0.66 |
| CLEROSTEROL | 0.43 |
| β SITOSTEROL | 59.97 |
| (NK) | 0.47 |
| SITOSTANOL | 0.31 |
| Δ5 AVENASTEROL | 1.53 |
| Δ5-24 STIGMASTADIENOL | 0.47 |
| (NK) | 0.25 |
| Δ7 STIGMASTENOL | 25.15 |
| Δ7 AVENASTEROL | 2.63 |
| TOTAL STEROLS PPM | 6574 |

PPM = PARTS PER MILLION
NK = NOT KNOWN (UNIDENTIFIED)

Analysis of the Triterpene Alcohols

An analysis for the presence of triterpene alcohols in cranberry seed oil was performed and three major components were found (see Table 12). Two components were determined to be pentacyclic triterpene alcohols (having retention times of 1.36 and 1.50) and one component was determined to be tetracyclic triterpene alcohol (having a retention time of 1.65).

Mass spectral features of the first triterpene alcohol identified were: 426 (M$^+$, 7%), 411 (M-Me, 17%), 393 (M-Me-H$_2$O, 3%), 218 (M-H$_2$O—C$_{14}$H$_{22}$, 100%), 203 (218-Me, 52%), 189 (218-C$_2$H$_5$, 16%). This compound was determined to be β-amyrin.

Mass spectral features of the second triterpene alcohol were: 426 (M$^+$, 8%), 411 (M-Me, 8%), 393 (M-Me-H$_2$O, 13%), 218 (M-H$_2$O—C$_{14}$H$_{22}$, 100%), 203 (218-Me, 21%), 189 (218-C$_2$H$_5$, 30%). This compound was determined to be α-amyrin.

Mass spectral features of the third triterpene alcohol were: 440 (M$^+$, 16%), 422 (M-Me, 41%), 407 (M-Me-H$_2$O, 100%), 379 (M-H$_2$O—C$_3$H$_7$, 55%), 300 (Me-C$_9$H$_{17}$, 25%), 313 (M-C$_9$H$_{17}$-2H, 3%), 273 (M-C$_{12}$H$_{22}$—H, 22%), 255 (273-H$_2$O, 24%). This compound was determined to be 24-methylene parkeol.

Figure 7:
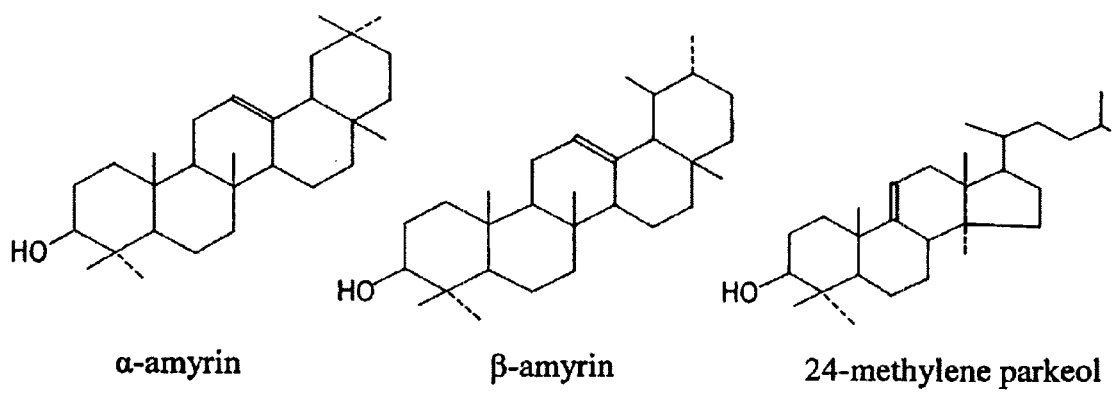
FIG. 7 shows the chemical structure of three major triterpene alcohols in cranberry seed oil, β-amyrin, α-amyrin, and 24-methylene parkeol.

The relative amounts of the triterpene alcohols were determined to be 9.9% for β-amyrin, 44.8% for α-amyrin, and 45.3% for 24-methylene parkeol. The chemical structure for each of the three major triterpene alcohols identified in cranberry seed oil is shown in FIG. 7.

TABLE 12

ANALYSIS OF THE ALCOHOLS IN CRANBERRY SEED OIL

| TOTAL ALCOHOLS (ppm) | 20.53 |
|---|---|
| C22% CH$_2$(CH$_{21}$)OH | 32.29 |

TABLE 12-continued

ANALYSIS OF THE ALCOHOLS IN CRANBERRY SEED OIL

| | |
|---|---|
| C24% | 26.06 |
| C25% | 1.95 |
| C26% | 13.88 |
| C27% | 3.17 |
| C28% | 22.65 |
| TOTAL TRITERPENE ALCOHOLS (ppm) | 1422.1 |
| COMPOSITION OF TRITERPENE ALCOHOLS | % |
| 1 NK | 0.28 |
| 2 NK | 0.54 |
| β AMYRIN | 1.90 |
| 4 NK | 13.16 |
| BUTYROSPERMOL | 0.72 |
| 6 NK | 6.64 |
| 7 NK | 1.03 |
| 8 NK | 1.78 |
| CYCLOARTENOL | 17.22 |
| 10 NK | 0.23 |
| 11 NK | 0.92 |
| 12 NK | 0.06 |
| 24 METHYLENEPARKEOL | 1.41 |
| 24 METYLENECYCLOARTENOL | 13.55 |
| 15 NK | 0.19 |
| 16 NK | 3.67 |
| 17 NK | 5.35 |
| CITROSTADIENOL | 29.49 |
| 19 NK | 0.24 |
| 20 NK | 0.94 |
| 21 NK | 0.25 |
| 22 NK | 0.43 |

NK = Not known (unidentified)
ppm = parts per million

Analysis of the Phenolic Compounds

The phenolic compounds in the cranberry seed oil of the invention were determined using HPLC, MS, and UV spectral analysis. An initial analysis indicated that only small amounts of phenolic compounds were present. Accordingly, a larger sample of oil was used to improve detection and identification. Specifically, a 20 g sample dissolved in hexane (912.5 ml) was extracted with methanol/water (80/20 v/v) three times (12.5 ml each) and centrifuged. Next, the extract samples were dried in a rotary evaporator and the remaining residue was resuspended in 10 ml of methanol/water for separation by high performance liquid chromatography (HPLC) and identification by liquid chromatographic (LC)–electrospray negative mass spectrometry.

The following HPLC parameters were employed: SPHERISORB ODS-2 column, length 25 cm; i.d. 4 mm; detector DIODE ARRAY from 200 nm to 400 nm; linear gradient from 90% A (water—0.5% $H_3PO_4$), 10% B (acetic acid-methanol (50-50 v/v) to 50% A B in 40', to 100% B in 60'. The chromatogram was monitored at 280 nm. For quantitative analysis, 4-hydroxy-3-methoxycinnamic acid was used as internal standard.

Figure 8:
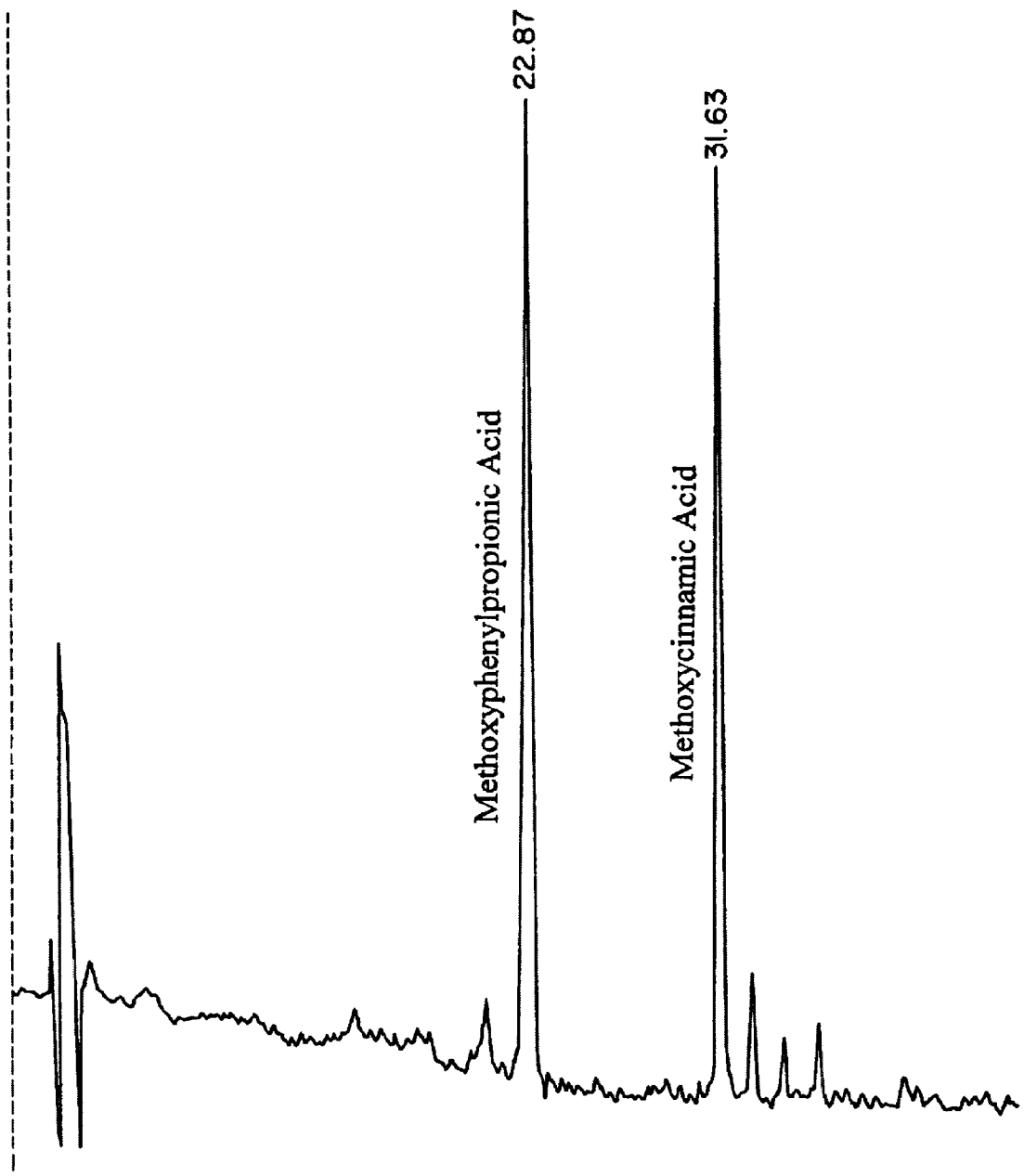
FIG. 8 shows the results of a high performance liquid chromatography (HPLC) analysis of two phenolic compounds in cranberry seed oil, methoxyphenylpropionic acid and methoxycinnamic acid.
Figure 9:
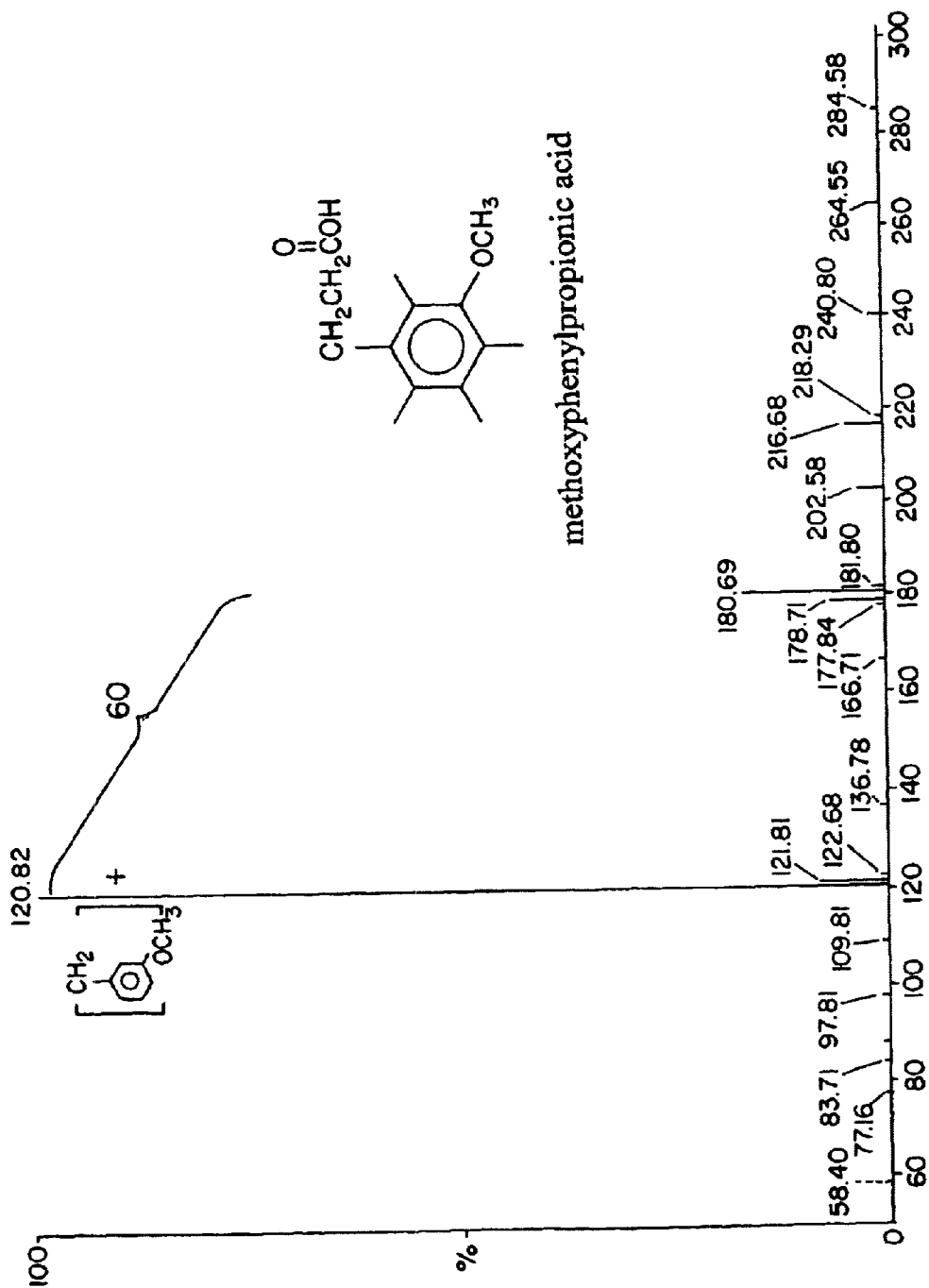
FIG. 9 shows a mass spectrum analysis of the phenolic compound methoxyphenylpropionic acid found in cranberry seed oil and the chemical structure of the compound methoxyphenylpropionic acid (insert panel).

Using the above methods of analysis, two major phenolic components were identified. The first component showed a specific absorption at 274 nm in UV analysis spectra (FIG. 8) had a shorter retention time than the second component (in reverse phase it is an index of more polarity), and, when subjected to electrospray negative mass spectrometry, gave a peak at m/z 180.69 (molecular ion), and with different cone voltage gave two important fragments at m/z 120.82 and at m/z 76.91 as shown in FIG. 9. Based on these the above findings, this compound was provisionally identified as methoxyphenylpropionic acid with the chemical structure indicated in FIG. 7.

Figure 10:
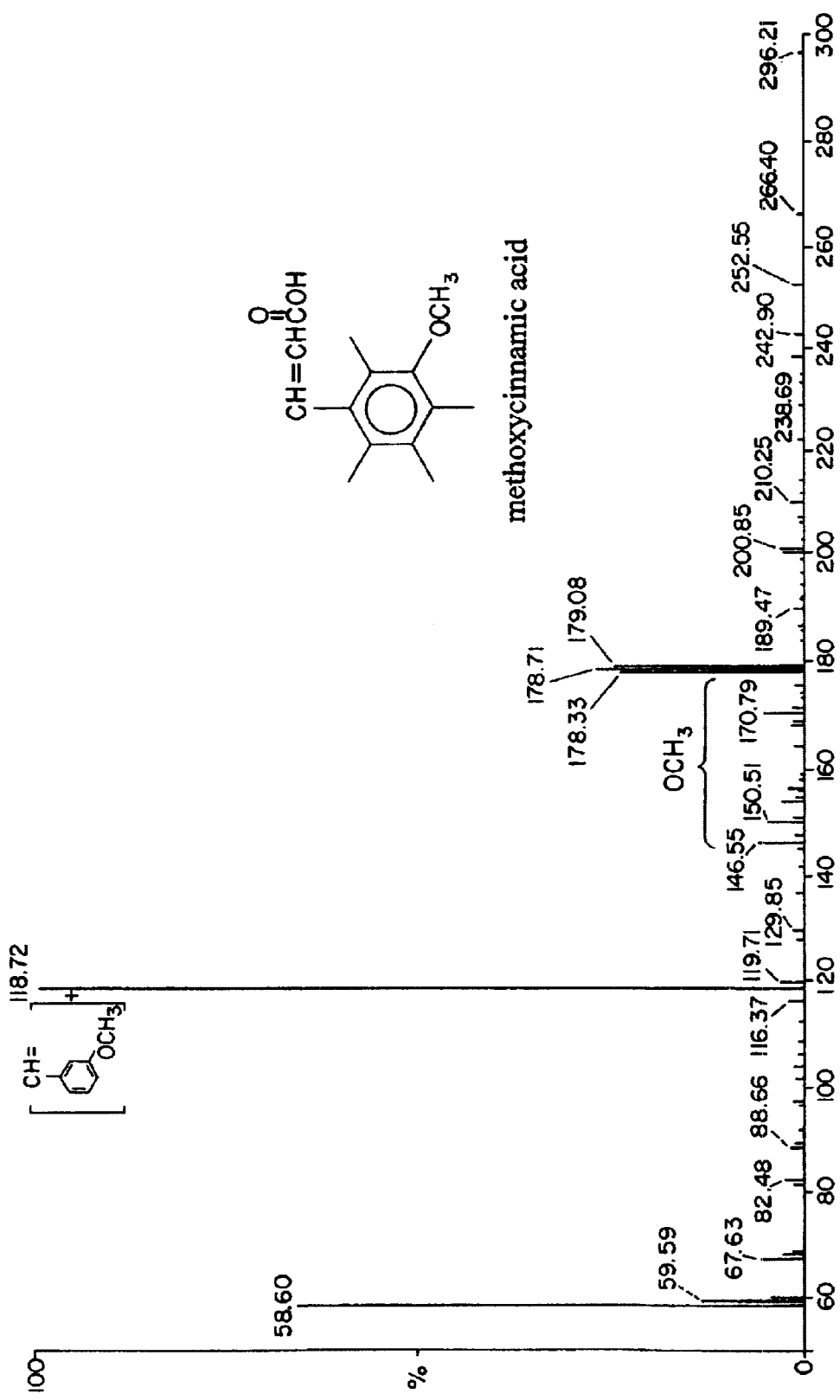
FIG. 10 shows a mass spectrum analysis of the phenolic compound methoxycinnamic acid found in cranberry seed oil and the chemical structure of the compound methoxycinnamic acid (insert panel).

The second predominant phenolic component identified in cranberry seed oil showed a specific absorption at 276 nm in UV analysis spectra (FIG. 8), and in electrospray negative mass spectrometry, had a molecular ion at m/z 178.71. In addition, this component displayed a principal fragment at m/z 118.72 as shown in FIG. 10. This compound was identified as methoxycinnamic acid with the chemical structure shown in FIG. 10.

Relative to the internal standard used, the concentrations of methoxyphenylpropionic acid and methoxycinnamic acid in cranberry seed oil were determined to be 1.8 ppm and 1.4 ppm, respectively.

Analysis of the Tocochromanols

Cranberry seed oil of the invention was analyzed for the presence of tocochromanols, a class of compounds that includes both tocopherols and tocotrienols. The method used for quantitating these compounds is based on the ability of these compounds to reduce the ferric ions ($Fe^{3+}$) to ($Fe^{2+}$). In particular, tocochromanols in the presence of certain reagents (e.g., orthophenantroline) form an orange complex, the intensity of which can be measured by visible spectrometry conducted at 510 nm. Further, absorption intensity is proportional to concentration, thus allowing for a determination of the amount of compound present in the sample.

Separation of individual tocopherols and tocotrienols was carried out using high performance liquid chromatography according to the method of Carpenter (Carpenter, Jr., A. P. *J. Amer. Oil Chemists's Soc.*, 56:668 (1979)). Detecting particular tocopherols or tocotrienols was conducted using UV absorption at 295 nm and identification was achieved by performing a comparison of retention times for the unknown components against known standards.

The qualitative and quantitative results of the analysis of the tocopherol and tocotrienol components of cranberry seed oil are given in Table 13 below. In comparison to the values reported in the literature for other oils (Table 2), cranberry seed oil is unique in its extremely high content of tocotrienols. The structure of each of the major isomers of tocopherols and tocotrienols is provided in FIG. 11.

TABLE 13

Quantitative Analysis of Tocopherols and Tocotrienols

| | Rel. Retention time | % | mg.kg$^{-1}$ |
|---|---|---|---|
| α-tocopherol (α) | 1.00 | 6.6 | 131 |
| α-tocotrienol (αT3) | 1.07 | 9.1 | 181 |
| γ-tocopherol (γ) | 142 | 5.6 | 112 |
| γ-tocotrienol (γT3) | 1.58 | 75.5 | 1505 |
| δ-tocopherol (δ) | 1.95 | 0.8 | 16 |
| δ-tocotrienol (δT3) | 21.9 | 2.4 | 48 |

Summary

The determinations described above reveal that the cranberry seed oil of the invention has a remarkably high amount of α-linolenic acid (~33%). Only flaxseed oil contains a higher amount (~50%) of this omega-3 fatty acid; two oils, i.e., soybean and rapeseed, contain ~7%; all other edible oils contain less than 2%.

In addition, and in contrast to flaxseed oil, cranberry seed oil also contains an equally high amount of the omega-6 fatty acid, linoleic (~38%). Further, stereo-chemical analysis of cranberry seed oil fatty acids indicated that the, β-position is rich in oleic (omega-9), linoleic (omega-6), and linolenic (omega-3) acids.

In addition, the above determinations show that cranberry seed oil is relatively rich in sterols, and triterpene alcohols, in particular, α- and β-amyrins, and 24-methyleneparkeol.

EXAMPLE 4

In Vitro Assay Demonstrating the Anti-Cancer Properties of a Cranberry Seed Oil Extract The following studies were performed to examine the anti-cancer properties of cranberry seed oil extracts.

Two independently derived cranberry seed oil extracts (OS96 and OS97) were test for their ability to inhibit the growth of two different human breast cancer cell lines (i.e., MDA-MB-435 and MCF-7). In each case, the extracts of the invention demonstrated the ability to inhibit the growth of each tumor cell line with greater growth inhibition being seen against the estrogen receptor positive cell line MCF-7.

The in vitro assay was performed as follows. First, the human breast cancer cell lines MDA-MB435 (estrogen receptor-negative) and MCF-7 (estrogen receptor-positive) were cultured under standard conditions using, minimum essential medium (alpha modification, 3.7 gm of sodium bicarbonate per liter, 10% v/v fetal calf serum). Media for culturing MCF-7 cells was further supplemented with 1 mM sodium pyruvate, 10 ug/mL insulin, 1% v/v fungizone (antibiotic/antimycotic, 10,000 units/mL penicillin G sodium, 10,000 ug/mL streptomycin sulphate and 25 ug/mL amphotericin B in 0.85% saline)).

Next, cells were plated at a density of $2 \times 10^4$ cells/well in 96-well, flat-bottomed tissue culture plates in a total volume of 200 uL of medium and incubated at 37° C., with or without the cranberry seed oil extracts. The plates were incubated for 48 hours at 37° C. and [3H] thymidine was then added to determine the number of dividing cells at each concentration of cranberry seed oil extract. The cells were reincubated for 4 hours, after which the medium and excess radiolabel were removed and cells were harvested and assayed for incorporated radioactivity as a measure of cell proliferation. Accordingly, the percentage of dividing cells was determined by comparing the number of disintegrations per minute of the treated cells (average of 3 wells/concentration) with that obtained for the control cells. The concentrations at which 50% and 90% growth inhibition occurred was determined as the IC50 & IC90 for each extract. Results are presented in Table 14 and represent the average of 3 experiments±SEM.

In summary, both the OS96 and OS97 cranberry seed oil extracts of the invention exhibited potent growth inhibition of the tumor cell lines tested.

TABLE 14

The effect of cranberry seed oil extracts (OS96 and OS97) on the human breast cancer cell lines MDA-MB-435 (estrogen-receptor negative) and MCF-7 (estrogen-receptor positive)

| Extract | IC50 (ug/mL) | IC90 (ug/mL) |
| --- | --- | --- |
| MDA-MB-435 | | |
| OS96 | 62.5 ± 4.5 | 82.9 ± 5.3 |
| OS97 | 15.6 ± 1.1 | 29.4 ± 1.9 |
| MCF-7 | | |
| OS96 | 32.6 ± 2.1 | 43.7 ± 2.6 |
| OS97 | 7.8 ± 0.4 | 12.4 ± 0.8 |

EXAMPLE 5

In Vitro Assay Demonstrating the Cholesterol Lowering Potential of Cranberry Seed Oil Extract The following studies were performed to examine the cholesterol lowering properties of cranberry seed oil extracts are demonstrated.

Two independently derived cranberry seed oil extracts (OS96 and OS97) were test for their cholesterol-lowering potential using a human liver cell line (HepG2). At least one of the tested extracts demonstrated the ability to reduce the amount of apoB secreted from the human liver cells. This was taken as a indication that the cranberry seed oil extracts of the invention are capable of causing beneficial changes in liver function relating to cholesterol metabolism.

The human liver cells (i.e., hepatoma HepG2 cells) of this example are known to secrete and catabolize lipoproteins similar to LDL and have been used as a model of human liver function relating to cholesterol metabolism. Thus, the ability the cranberry seed oil extracts of the invention to change HepG2 secretion of lipoproteins was assayed in order to determine if the extracts of the invention have cholesterol lowering potential. The assay was performed as follows. First, Hep2G cells were cultured in minimum essential medium (supplemented with 10% fetal bovine serum or 1% bovine serum prior to experimentation) and co-cultivated with a negative control extract (bovine serum albumin) or increasing concentrations (25–200 ug/mL) of cranberry seed oil extract made up in the same carrier liquid. After 24 hours of exposure to the extracts, the cell media was assayed for the presence of apolipoprotein B using an enzyme-linked immunosorbent assay (ELISA). In particular, cells were washed and dissolved in 0.1 N NaOH for protein determination and the apo B content of the medium was calculated in ug per mg of cell protein and expressed as percent of control (medium of cells incubated with DMSO) and these results are presented in Table 15.

The results show that increasing concentrations of the OS96 extract caused a dose-dependent reduction of apo B in the cell medium. The highest dose of OS96 (200 ug/mL) extract significantly lowered apo B in the medium by 34%. The apo B-lowering effect produced by the remaining doses was non-significant. In contrast, OS97 did not significantly affect levels of apo B in the medium at any concentration tested.

Thus, in at least one extract (OS96), a significant cholesterol lowering potential was observed as measured by a reduction in apo B levels in human liver cells. Moreover, using a MTT assay to assess cell viability, it was determined that none of the cranberry seed oil extract dosages tested were toxic to cells.

TABLE 15

Changes in overall apo B production in HepG2 cells exposed to increasing concentrations of cranberry seed oil extracts

| Extract | N | Conc, ug/mL | Percent apo B in medium |
| --- | --- | --- | --- |
| OS96 | 4 | 0 | 100 ± 6 |
| OS96 | 4 | 200 | 66 ± 9 |
| OS96 | 4 | 100 | 71 ± 17 |
| OS96 | 4 | 50 | 83 ± 7 |
| OS96 | 4 | 25 | 92 ± 7 |
| OS97 | 4 | 0 | 100 ± 13 |
| OS97 | 4 | 200 | 80 ± 16 |
| OS97 | 4 | 100 | 93 ± 10 |
| OS97 | 4 | 50 | 84 ± 7 |
| OS97 | 4 | 25 | 100 ± 20 |

Means ± SEM.
* = significant different from control, $p < 0.05$

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated cranberry seed oil produced by a method comprising, physically disrupting cranberry seeds under conditions that reduce the temperature and exposure to oxygen of the seeds relative to the temperature and exposure to oxygen which would occur in the absence of such conditions;

adding to the seeds an organic solvent to produce an extract/solvent mixture; and removing the solvent portion of the extract/solvent mixture thereby producing isolated cranberry seed oil substantially free of solvent.

2. The isolated oil of claim 1 substantially free of impurities.

3. The isolated oil of claim 2, comprising tocochromanol selected from the group consisting of a α-tocopherol, γ-tocopherol, δ-tocopherol, α-tocotrienol, γ-tocotrienol, δ-tocotrienol, or a combination thereof.

4. The isolated oil of claim 1, further comprising an exogenous flavonoid, tamoxifen, or a combination thereof.

5. The isolated oil of claim 1, comprising a compound selected from the group consisting of α-linolenic acid (omega-3), oleic acid (omega-9), linoleic acid (omega-6), β-sitosterol, schottenol, α-amyrin, β-amyrin, 24-methyleneparkeol, methoxyphenylpropionic acid, methoxycinnamic acid, or a combination thereof.

6. The isolated oil of claim 2, in a form suitable for use in a foodstuff.

7. The isolated oil of claim 2, in a form suitable for use as a dietary supplement.

8. The isolated oil of claim 2, in a form suitable for use in a pharmaceutical composition.

9. A foodstuff comprising the oil of claim 2.

10. A dietary supplement comprising the oil of claim 2.

11. A pharmaceutical composition comprising the oil of claim 2.